(12) United States Patent
Smith et al.

(10) Patent No.: US 6,370,939 B2
(45) Date of Patent: *Apr. 16, 2002

(54) APPARATUS AND METHOD FOR MEASUREMENT OF MASS AND HEAT FLOW CHANGES

(76) Inventors: Allan L. Smith, 328 Pembroke Rd., Bala Cynwyd, PA (US) 19004; Ingemar Wadso, Blackhornsvagen 6, 224-67 Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/785,773

(22) Filed: Feb. 16, 2001

Related U.S. Application Data

(63) Continuation of application No. 09/204,656, filed on Dec. 2, 1998, now Pat. No. 6,189,367.
(60) Provisional application No. 60/067,239, filed on Dec. 2, 1997.

(51) Int. Cl.[7] ............................ G01N 29/02; G01N 9/00; G01K 17/00; G01K 13/00
(52) U.S. Cl. ................... 73/19.03; 73/24.06; 73/30.04; 73/31.06; 73/32 A; 73/54.41; 73/61.49; 73/61.75; 73/61.79; 73/64.53; 374/31; 374/142; 374/43
(58) Field of Search ............................ 374/31, 142, 43, 374/45, 32, 35; 73/204.12, 204.26, 580, 862.59, 24.01, 19.03, 24.03, 24.06, 25.03, 25.01, 31.05, 31.06, 32 A, 61.45, 61.46, 61.49, 61.62, 61.75, 61.76, 651, 61.79, 64.53, 30.04, 54.24, 54.41, 54.42, 64.42

(56) References Cited

U.S. PATENT DOCUMENTS

| | | | | |
|---|---|---|---|---|
| 3,863,495 A | * | 2/1975 | Schulz | 73/61.1 |
| 3,926,271 A | * | 12/1975 | Patashnick | 177/210 |
| 4,596,697 A | * | 6/1986 | Ballato | 422/98 |
| 5,201,215 A | * | 4/1993 | Granstaff et al. | 73/54.41 |
| 5,798,452 A | * | 8/1998 | Martin et al. | 73/32 R |
| 6,106,149 A | * | 8/2000 | Smith | 374/31 |
| 6,189,367 B1 | * | 2/2001 | Smith et al. | 73/19.03 |
| 6,190,035 B1 | * | 2/2001 | Smith | 374/31 |

* cited by examiner

Primary Examiner—Hezron Williams
Assistant Examiner—Rose M. Miller
(74) Attorney, Agent, or Firm—Sampson & Associates

(57) ABSTRACT

Provided are a measurement apparatus and a measurement system comprising sample and reference microresonators, such as sample and reference quartz crystal microbalances; sample and reference heat flow sensors; and a heat sink coupled thermally to the heat flow sensors. These may be used to measure changes in one or more properties, such as mass, due to a liquid sample on a surface of a sample microresonator and also to measure heat flows from the sample on the surface of the sample microresonator by utilizing the heat flow sensors, which are coupled thermally to the corresponding sample or reference microresonators. Also provided is a method for measuring one or more properties, such as mass, of a liquid sample and the flow of heat from the sample to the heat sink by utilizing such apparatus.

22 Claims, 19 Drawing Sheets

FIG. 1
*PRIOR ART*
$$\begin{cases} Q = C\Delta T \\ Q = \int (dQ/dt)\, dt \end{cases}$$

$$P = \frac{1}{S}\left[U + \tau\left(\frac{dU}{dt}\right)\right]$$

FIG. 2
*PRIOR ART*

APPARATUS AND METHOD FOR MEASUREMENT OF MASS AND HEAT FLOW CHANGES

RELATED APPLICATION

This application claims priority to U.S. Provisional Patent Application No. 60/067,239, filed Dec. 2, 1997, and is a continuation of U.S. patent application Ser. No. 09/204,656, filed Dec. 2, 1998 is now U.S. Pat. No. 6,189,367, the contents of which are incorporated herein by reference in their entirety.

FIELD OF THE INVENTION

The present invention pertains generally to the field of sensors for the measurement of changes in mass and heat flow. More particularly, the present invention pertains to multiple microresonator mass and heat flow sensors which may provide simultaneous and continuous measurement of the changes in mass and heat flow at a gas-solid interface. The present invention also pertains to an apparatus comprising such sensors as sample and reference sensors, and to methods of measuring the mass and heat flow of a gas, liquid, or solid sample by utilizing such apparatus.

BACKGROUND OF THE INVENTION

Although the piezoelectric effect has been known since the 19th century, the development of quartz crystal devices which oscillate at precisely defined resonant frequencies and which can be incorporated as passive elements into electronic instruments began in the 1920's. Like much of our modem electronic technology, their development received a massive push during World War II, when over 30 million quartz crystal oscillators were produced for use in military communications equipment. Today there is widespread use of quartz crystal oscillators and of new types of microresonators in electronics wherever precise control of frequency is needed as, for example, in radio frequency communications, in frequency meters and timepieces, in scientific instrumentation, and in computers and cellular telephones.

There are several useful books which describe the physics of quartz crystal oscillators and other microresonators and their use in electronic circuits. For example, *Introduction to Quartz Crystal Unit Design* by Bottom, Van Nostrand Reinhold, New York, 1982, discusses the physical crystallography of quartz, mechanic vibrations and stress/strain relationships, the piezoelectric effect, the equivalent circuit of the quartz resonator and its use as a circuit component, the temperature stability of quartz oscillators, and other topics of importance in the application of these devices. *Science*, Vol. 249, pages 1000–1007 (1990), by Ward et al., describes the converse piezoelectric effect and its use in in-situ interfacial mass detection, such as in thickness monitors for thin-film preparation and in chemical sensors for trace gases. *Analytical Chemistry*, Vol. 65, pages 940A–948A and 987A–996A (1993), by Grate et al., compares the acoustical and electrical properties of five acoustic wave devices used as microsensors and transducers, including quartz crystal oscillators.

Any crystalline solid can undergo mechanical vibrations with minimum energy input at a series of resonant frequencies, determined by the shape and size of the crystal and by its elastic constants. In quartz, such vibrations can be induced by the application of a radio frequency voltage at the mechanical resonant frequency across electrodes attached to the crystal. This is termed the inverse piezoelectric effect. The thickness shear mode is the most common mechanical vibration used in quartz crystal oscillators. A typical commercially available quartz crystal oscillator is a thin circular quartz plate, cut from a single crystal at an angle of 37.25° with respect to the crystal's z axis (the so-called "AT cut"). This angle is chosen so that the temperature coefficient of the change in frequency is, to the first approximation, zero at 25° C., thus minimizing the drift in resonant frequency with ambient temperature change. A slight change in the cut angle produces crystals with zero temperature coefficients at elevated temperatures. The AT-cut plate has thin film electrodes on most of the top and bottom surfaces of the crystal, and is supported in various ways at its circumference or perimeter. Both the fundamental and the first few overtones of the thickness shear mode have been utilized in crystal oscillators. A typical AT-cut quartz disk piezoid operating at a 10.8 MHz fundamental has the following dimensions, according to page 99 of the above-mentioned reference by Bottom:

| | |
|---|---|
| diameter: | 8.0 mm |
| electrode diameter: | 2.5 mm |
| blank thickness: | 0.154 mm |

The quality factor, Q, defined for any resonant circuit incorporating quartz crystal oscillators is usually not less than $10^5$ and may be as high as $10^7$. With careful attention to the control of temperature in a vacuum environment, a short-term frequency stability of one part in $10^{10}$ can be obtained, although the stated short-term stability for commercial units is ±3 ppm.

The resonant frequency of a quartz crystal oscillator is inversely proportional to the thickness, e, of the plate. For a circular disk, $f = nK/e$ where n=1, 3, 5, ... and K is the frequency constant (for example, see page 134ff of the above-mentioned reference by Bottom). For an AT-cut disk, K=1664 kHz mm, so that a disk of a thickness of 1 mm will oscillate at 1,664 MHz. If this thickness is increased by the deposition of material on the surface of the quartz crystal oscillator, then its frequency will decrease.

In 1957, Sauerbrey in *Z. Physik*, Vol. 155, 206 (1959), derived the fractional decrease in frequency f of a circular disk quartz crystal oscillator upon deposition of a mass, m, of material on its surface. The derivation relies on the assumption that a deposited foreign material exists entirely at the anti-node of the standing wave propagating across the thickness of the quartz crystal, so that the foreign deposit can be treated as an extension of the crystal, as, for example, described in *Applications of Piezoelectric Quartz Crystal Microbalances* by Lu et al., Elsevier, New York, 1984. Sauerbrey's result for the fundamental vibrational mode is as follows:

$$\Delta f / f_0 = -\Delta e / e_0 = -2 f_0 \Delta m / A \sqrt{\rho \mu}$$

Here, $\Delta e$ is the change in the original thickness $e_0$, A is the piezoelectrically active area, $\rho$ is the density of quartz, and $\mu$ is the shear modulus of quartz. By measuring the decrease in frequency, one thus can determine the mass of material deposited on the crystal. This is the principle of the quartz crystal microbalance. In practice, the assumptions underlying the Sauerbrey equation are valid for deposits up to about 10% of the crystal mass, although the sensitivity to mass has been shown experimentally to decrease from the center of the electrode to its edge.

Torres et al. in *J. Chem. Ed.*, Vol. 72, pages 67–70 (1995), describe the use of a quartz crystal microbalance to measure the mass effusing from Knudsen effusion cells at varying temperatures, in order to determine the enthalpies of sublimation. They reported a sensitivity of about $10^8$ g/sec in the mass deposition rate. The application of the quartz crystal microbalance in chemistry for the sensitive detection of gases adsorbed on solid absorbing surfaces has been reviewed by Alder et al., in *Analyst*, Vol. 108, pages 1169–1189 (1983) and by McCallum in *Analyst*, Vol. 114, pages 1173–1189 (1989). The quartz crystal microbalance principle has been applied to the development of thickness monitors in the production of thin films by vacuum evaporation, as, for example, described in the above-mentioned reference by Lu et al. Quartz crystal oscillators of various sizes and modes of vibration are commonly used currently in research efforts in sensor development.

Throughout this application, various publications and patents are referred to by an identifying citation. The disclosures of the publications and patents referenced in this application are hereby incorporated by reference into the present disclosure to more fully describe the state of the art to which this invention pertains.

U.S. Pat. No. 5,339,051 to Koehler et al. describes resonator-oscillators for use as sensors in a variety of applications. U.S. Pat. No. 4,596,697 to Ballato and U.S. Pat. No. 5,151,110 to Bein et al. describe coated resonators for use as chemical sensors.

To overcome the influences of temperature changes on the microresonators, U.S. Pat. No. 4,561,286 to Sekler et al. and U.S. Pat. No. 5,476,002 to Bower et al. describe active temperature control or the use of temperature sensors with the microresonators. U.S. Pat. No. 5,686,779 to Vig describes a microresonator for direct use as a thermal sensor.

Microresonators, including quartz crystal microbalances (QCM's), have been utilized to determine the mass changes with a variety of liquid samples such as, for example, described in U.S. Pat. No. 4,788,466 to Paul et al. When the microresonator is coated, chemicals present in the liquid samples may be detected as, for example, described in U.S. Pat. No. 5,306,644 to Myerholtz et al.

Microresonators have been adapted to measure the viscosity of a liquid sample as, for example, described in U.S. Pat. No. 4,741,200 to Hammerle. U.S. Pat. No. 5,201,215 to Granstaff et al. describes the use of microresonators to measure the mass of a solid and physical properties of a fluid in a sample.

Calorimeters for various types of heat measurements are well known as, for example, described in U.S. Pat. No. 4,492,480 to Wadso et al.; U.S. Pat. No. 5,295,745 to Cassettari et al.; and U.S. Pat. No. 5,312,587 to Templer et al. A combined scientific apparatus of a thermal analyzer, such as a calorimeter, and an X-ray diffractometer for observing simultaneously both thermodynamic and structural properties of materials is described in U.S. Pat. No. 4,821,303 to Fawcett et al.

Despite the various approaches proposed for the design of sensors and measurement systems based on microresonators as the sampling device, there remains a need for sensors and measurement systems which can simultaneously and continuously measure with high sensitivity and accuracy both mass and heat flow changes of a sample in contact with the microresonator.

SUMMARY OF THE INVENTION

One aspect of the present invention pertains to a new scientific apparatus based on the combination of two or more devices, wherein each device comprises (i) a microresonator mass sensor or microbalance, such as, for example, a quartz crystal microbalance (QCM), which may be used to measure very small changes of mass at its surface; and, (ii) a heat flow sensor, such as, for example, an isothermal heat conduction calorimeter (HCC), which may be used to measure small heat flows; and wherein at least one combined microresonator and heat flow sensor device is utilized as a reference device and at least one combined microresonator and heat flow sensor device is utilized as a sample device to measure the sample. In one embodiment, the dual microresonator and heat flow sensor sample and reference apparatus measures simultaneously and continuously, with high sensitivity (nanogram in mass, sub-microwatt in heat flow), the changes in mass and heat flow at a small gas-solid interface, for example, about 1 $cm^2$ or less in area, due to chemical processes such as evaporation or condensation, adsorption or desorption, or gas-surface reactions. The new scientific apparatus of the present invention may be advantageously utilized in a variety of applications such as, for example, studying the hydration and dehydration of films of proteins and other biomolecules deposited on solid substrates, particularly for films utilized in biosensors, diagnostic immunoassays, the separation of proteins by chromatography, and as models for biological and biocompatible membranes and surfaces; studying the energetics of intermolecular interactions at the surface of polymer films and other organic surfaces important in adhesion, lubrication, wetting, and corrosion; and studying the energetics of the drying and curing of both water-based and organic solvent-based paints and finishes.

One aspect of the present invention pertains to a mass and heat flow measurement apparatus comprising (i) a sample sensor comprising a first microresonator, a first heat flow sensor, and a heat sink coupled thermally to the first heat flow sensor, wherein the first heat flow sensor is thermally coupled to the first microresonator; and further wherein the first microresonator is capable of measuring the mass of a sample in contact with the first microresonator, and the first heat flow sensor is capable of measuring the flow of heat from the sample to the heat sink; (ii) a reference sensor comprising a second microresonator, a second heat flow sensor coupled thermally to the second microresonator, and a heat sink coupled thermally to the second microresonator; and, (iii) a chamber housing the sample and reference sensors, wherein the reference sensor is isolated from the sample; and further wherein the second microresonator is capable of measuring a reference signal relating to mass at a surface of the second microresonator, and the second heat flow sensor is capable of measuring a reference signal relating to the flow of heat from the surface of the second microresonator to the heat sink coupled thermally to the second heat flow sensor. In one embodiment, the first microresonator comprises a piezoelectric substrate having a perimeter, a first face for directly contacting the sample, and a second opposite face isolated from contacting the sample; and further wherein the second microresonator comprises a piezoelectric substrate having a perimeter, a first face, and a second opposite face, the piezoelectric substrates of the first and second microresonators having a resonant frequency and capable of providing a measurement signal based on the resonant frequency. In one embodiment, the sample is a solid sample.

Suitable microresonators for the apparatus of this invention include, but are not limited to, bulk acoustic wave sensors, quartz crystal microbalances, surface acoustic wave sensors, flexural plate wave sensors, and acoustic plate mode sensors. In a preferred embodiment, the first and second microresonators of the apparatus of the present invention are quartz crystal microbalances. In one embodiment, the first microresonator comprises a surface coating with an affinity for at least one component of the sample. In one embodiment, the second microresonator comprises a surface coating with an affinity for at least one component of the sample.

In one embodiment, the first and second heat flow sensors of the apparatus of this invention comprise a thermopile.

Another aspect of the present invention pertains to a mass and heat flow measurement system comprising (i) at least one mass and heat flow measurement sample sensor comprising a microresonator, a heat flow sensor coupled thermally to the microresonator, and a heat sink coupled thermally to the heat flow sensor, wherein the microresonator generates data relating to the changes in mass on a surface of the microresonator arising from contacting the microresonator with a sample; and further wherein the heat flow sensor generates data relating to the changes in flow of heat from the sample to the heat sink from contacting the microresonator with the sample; (ii) at least one mass and heat flow measurement reference sensor comprising a reference microresonator, a reference heat flow sensor coupled thermally to the reference microresonator, and a heat sink coupled thermally to the reference heat flow sensor, wherein the microresonator of the reference sensor is not in contact with the sample; and further wherein the reference microresonator generates data relating to the changes in mass on a surface of the reference microresonator and the reference heat flow sensor generates data relating to the changes in flow of heat from the surface of the reference microresonator to the heat sink coupled thermally to the reference heat flow sensor; and, (iii) a measurement instrument capable of correlating the data from the sample and reference sensors so as to provide measurement of the mass of the sample and the flow of heat from the sample to the heat sink coupled thermally to the heat flow sensor of the sample sensor. In one embodiment of the system of this invention, the microresonator of the sample sensor comprises a piezoelectric substrate having a perimeter, a first face for directly contacting a sample, and a second opposite face isolated from contacting the sample; and further wherein the reference microresonator comprises a piezoelectric substrate having a perimeter, a first face, and a second opposite face, the piezoelectric substrates of the microresonator of the sample sensor and the reference microresonator having a resonant frequency and capable of providing a measurement signal based on the resonant frequency. In one embodiment, the sample is a solid sample.

Suitable microresonators for the sample sensor and suitable reference microresonators for the system of the present invention include, but are not limited to, bulk acoustic wave sensors, quartz crystal microbalances, surface acoustic wave sensors, flexural plate wave sensors, and acoustic plate mode sensors. In a preferred embodiment, the microresonator of the sample sensor and the reference microresonator are quartz crystal microbalances. In one embodiment, the microresonator of the sample sensor comprises a surface coating with an affinity for at least one component of the sample. In one embodiment, the reference microresonator comprises a surface coating with an affinity for at least one component of the sample.

In one embodiment, the heat flow sensor of the sample sensor and the reference heat flow sensor of the system of the present invention comprise a thermopile.

Another aspect of the present invention pertains to a method for measuring the mass of a sample and the flow of heat from the sample to a heat sink, which method comprises the steps of: (i) contacting the sample with a mass and heat flow measurement system, as described herein; (ii) obtaining data from both the sample and reference sensors of the mass and heat flow measurement system of the present invention; and, (iii) determining the mass of the sample and the flow of heat from the sample to the heat sink coupled thermally to the heat flow sensor of the sample sensor. In one embodiment, the sample is a solid sample, and, preferably, the method of this invention measures the enthalpy of sublimation of the solid sample.

Still another aspect of the present invention pertains to a mass and heat flow measurement apparatus comprising (i) a gas sample sensor comprising a first microresonator, a first heat flow sensor, and a heat sink coupled thermally to the first heat flow sensor, wherein the first heat flow sensor is thermally coupled to the first microresonator; and further wherein the first microresonator comprises a coated surface and is capable of measuring the changes in mass when a gas reacts with, is adsorbed, or is desorbed from the coated surface; and the first heat flow sensor is capable of measuring the flow of heat from the coated surface to the heat sink; (ii) a gas reference sensor comprising a second microresonator, a second heat flow sensor coupled thermally to the second microresonator, and a heat sink coupled thermally to the second microresonator; and, (iii) a chamber housing the gas sample and gas reference sensors, wherein the gas reference sensor is isolated from the gas in contact with the first microresonator; and further wherein the second microresonator is capable of measuring a reference signal relating to mass at a surface of the second microresonator, and the second heat flow sensor is capable of measuring a reference signal relating to the flow of heat from the surface of the second microresonator to the heat sink coupled thermally to the second heat flow sensor. In one embodiment, the chamber further comprises a gas input lead for introducing the gas into contact to the coated surface of the first microresonator and a gas output lead for removing the gas from contact to the coated surface of the first microresonator.

Yet another aspect of the present invention pertains to a mass and heat flow measurement system comprising (i) at least one mass and heat flow measurement gas sample sensor comprising a microresonator, a heat flow sensor coupled thermally to the microresonator, and a heat sink coupled thermally to the heat flow sensor, wherein the microresonator comprises a coated surface and generates data relating to the changes in mass on the coated surface of the microresonator arising from contacting the coated surface with a gas; and further wherein the heat flow sensor generates data relating to the changes in flow of heat from the coated surface to the heat sink from contacting the coated surface with the gas; (ii) at least one mass and heat flow measurement gas reference sensor comprising a reference microresonator, a reference heat flow sensor coupled thermally to the reference microresonator, and a heat sink coupled thermally to the reference heat flow sensor, wherein the microresonator of the gas reference sensor is not in contact with the gas in contact with the microresonator of the gas sample sensor; and further wherein the reference microresonator generates data relating to the changes in mass on a surface of the reference microresonator, and the reference heat flow sensor generates data relating to the changes in flow of heat from the surface of the reference microresonator to the heat sink coupled thermally to the reference heat flow sensor; and, (iii) a measurement instrument capable of correlating the data from the gas sample and gas reference sensors so as to provide measurement of the changes in mass on the coated surface of the microresonator of the gas sample sensor and the flow of heat from the coated surface to the heat sink coupled thermally to the heat flow sensor of the gas sample sensor. In one embodiment, the system further comprises a gas input lead for introducing the gas into contact to the coated surface of the microresonator of the gas sample sensor and a gas output lead for removing the gas from contact to the coated surface of the microresonator of the gas sample sensor.

Another aspect of the present invention pertains to a method for measuring the change in mass and flow of heat from a coated surface to a heat sink when a gas reacts with, is adsorbed, or is desorbed from the coated surface, which method comprises the steps of: (i) contacting the gas with a mass and heat flow gas measurement system, as described herein; (ii) obtaining data from both the gas sample and gas reference sensors of the mass and heat flow gas measurement system of this invention; and, (iii) determining the changes in mass and the flow of heat from the coated surface of the microresonator of the gas sample sensor to the heat sink coupled thermally to the heat flow sensor of the gas sample sensor, which changes arise when the gas reacts with, is adsorbed, or is desorbed from the coated surface. In one embodiment of the method, the mass and heat flow gas measurement system further comprises a gas input lead for introducing the gas to the microresonator of the gas sample sensor and a gas output lead for removing the gas from contact to the microresonator of the gas sample sensor. In one embodiment, the method measures the molar heat of adsorption of the gas, and, preferably, the molar heat of adsorption is measured in real time. In one embodiment, the reference microresonator comprises a coated surface. In one embodiment, the coated surface of the reference microresonator comprises the same coating as the coated surface of the microresonator of the gas sample sensor. In one embodiment, the method measures the molar heat of reaction of the gas with the coated surface, and, preferably, the molar heat of reaction is measured in real time. In one embodiment, the method measures the molar heat of desorption of the gas, and, preferably, the molar heat of desorption is measured in real time. In one embodiment, the microresonator of the gas sample sensor and the reference microresonator are selected from the group of microresonators consisting of: bulk acoustic wave sensors, quartz crystal microbalances, surface acoustic wave sensors, flexural plate wave sensors, and acoustic plate mode sensors. In a preferred embodiment, the microresonator of the gas sample sensor and the reference microresonator are quartz crystal microbalances.

Another aspect of the present invention pertains to a heat flow measurement apparatus comprising (i) a liquid sample sensor comprising a first microresonator, a first heat flow sensor, and a heat sink coupled thermally to the first heat flow sensor, wherein the first heat flow sensor is thermally coupled to the first microresonator; and further wherein the first microresonator is capable of measuring a signal relating to mass at a surface of the first microresonator, and the first heat flow sensor is capable Of measuring the flow of heat from a liquid sample disposed on the first microresonator to the heat sink; (ii) a liquid reference sensor comprising a second microresonator, a second heat flow sensor coupled thermally to the second microresonator, and a heat sink coupled thermally to the second microresonator; and, (iii) a chamber housing the liquid sample and liquid reference sensors, wherein the liquid reference sensor is isolated from the liquid sample in contact with the first microresonator; and further wherein the second microresonator is capable of measuring a reference signal relating to mass at a surface of the second microresonator, and the second heat flow sensor is capable of measuring a reference signal relating to the flow of heat from the surface of the second microresonator to the heat sink coupled thermally to the second heat flow sensor. In one embodiment of the heat flow apparatus of this invention, the chamber further comprises a liquid input lead for introducing the liquid sample into contact to the first microresonator. In one embodiment, the first microresonator is capable of measuring the mass of the liquid sample in contact with the first microresonator.

Still another aspect of this invention pertains to a heat flow measurement system comprising (i) at least one heat flow measurement liquid sample sensor comprising a microresonator, a heat flow sensor coupled thermally to the microresonator, and a heat sink coupled thermally to the heat flow sensor, wherein the microresonator is capable of measuring a signal relating to mass at a surface of the microresonator; and further wherein the heat flow sensor generates data relating to the changes in the flow of heat from a liquid sample to the heat sink from contacting the microresonator with the liquid sample; (ii) at least one heat flow measurement liquid reference sensor comprising a reference microresonator, a reference heat flow sensor coupled thermally to the reference microresonator, and a heat sink coupled thermally to the reference heat flow sensor, wherein the microresonator of the reference sensor is not in contact with the liquid sample in contact with the microresonator of the liquid sample sensor; and further wherein the reference microresonator is capable of measuring a reference signal relating to mass at a surface of the reference microresonator, and the reference heat flow sensor generates data relating to the changes in flow of heat from the surface of the reference microresonator to the heat sink coupled thermally to the reference heat flow sensor; and, (iii) a measurement instrument capable of correlating the data from the liquid sample and liquid reference sensors so as to provide measurement of the flow of heat from the liquid sample to the heat sink coupled thermally to the heat flow sensor of the liquid sample sensor. In one embodiment of the heat flow measurement system of the present invention, the system further comprises a liquid input lead for introducing the liquid sample to the microresonator of the liquid sample sensor. In one embodiment, the microresonator of the liquid sample sensor generates data relating to the changes in mass on a surface of the microresonator of the liquid sample sensor, which data arises from contacting the microresonator of the liquid sample sensor with the liquid sample; wherein the reference microresonator generates data relating to the changes in mass on a surface of the reference microresonator; and further wherein the measurement instrument is capable of correlating the data from the liquid sample and liquid reference sensors so as to further provide measurement of the mass of the liquid sample. In one embodiment, the mass of the liquid sample is known.

Another aspect of the present invention pertains to a method for measuring the change in the flow of heat from a liquid sample to a heat sink, which method comprises the steps of: (i) contacting the liquid sample with a heat flow measurement system, as described herein; (ii) obtaining data from both the liquid sample and liquid reference sensors of the heat flow measurement system of this invention; and, (iii) determining the flow of heat from the liquid sample to the heat sink Coupled thermally to the heat flow sensor of the liquid sample sensor. In one embodiment, the heat flow measurement system further comprises a liquid input lead for introducing the liquid sample to the microresonator of the liquid sample sensor. In one embodiment, the microresonator of the liquid sample sensor generates data relating to the changes in mass on a surface of the microresonator of the liquid sample sensor, which data arises from contacting the microresonator of the liquid sample sensor with the liquid sample; wherein the reference microresonator generates data relating to the changes in mass on a surface of the reference microresonator; and further wherein the measurement instrument is capable of correlating the data from the liquid sample and liquid reference sensors so as to further provide measurement of the mass of the liquid sample. In one embodiment, the mass of the liquid sample is known. In one embodiment, the method measures the molar heat of evaporation of the liquid sample. In one embodiment, the microresonator of the liquid sample sensor comprises a coated surface, and, preferably, the reference microresonator also comprises a coated surface, and, most preferably, the coated surface of the reference microresonator comprises the same coating as the coated surface of the microresonator of the liquid sample sensor. In one embodiment, the microresonator of the liquid sample sensor and the reference microresonator are selected from the group of microresonators consisting of: bulk acoustic wave sensors, quartz crystal microbalances, surface acoustic wave sensors, flexural plate wave sensors, and acoustic plate mode sensors. In a preferred embodiment, the microresonator of the liquid sample sensor and the reference microresonator are quartz crystal microbalances.

As one skilled in the art will appreciate, features of one embodiment and aspect of the invention are applicable to other embodiments and aspects of the invention.

BRIEF DESCRIPTION OF THE DRAWINGS

The foregoing summary, as well as the following detailed description of embodiments of the invention, will be better understood when read in conjunction with the appended drawings. For the purpose of illustrating the invention, particular arrangements and methodologies are shown in the drawings. It should be understood, however, that the invention is not limited to the precise arrangements shown or to the methodologies of the detailed description.

FIG. 1 illustrates the contrast between the functionality of an adiabatic calorimetry versus a heat conduction calorimetry.

FIG. 2 shows the basic equations for heat conduction calorimetry.

DETAILED DESCRIPTION OF THE INVENTION

The combined microresonator and heat flow sensor sample and reference devices of the present invention provide a new apparatus and method in thermal analysis and calorimetry. This new apparatus and method provide the capability of measuring the change in heat flow and mass at a gas-solid interface as the compositions of both the gas phase and the solid surface change. In thermodynamic terms, the combined microresonator and heat flow sensor sample and reference devices are capable of measuring directly the partial molal enthalpy of a volatile component, i, of a film on a surface, as the other non-volatile components and the temperature (T) and pressure (P) are held constant:

$$H_i = (\partial H / \partial n_i)_{T,P,nj}$$

where j is the number of moles of the total components (n).

Figure 3:
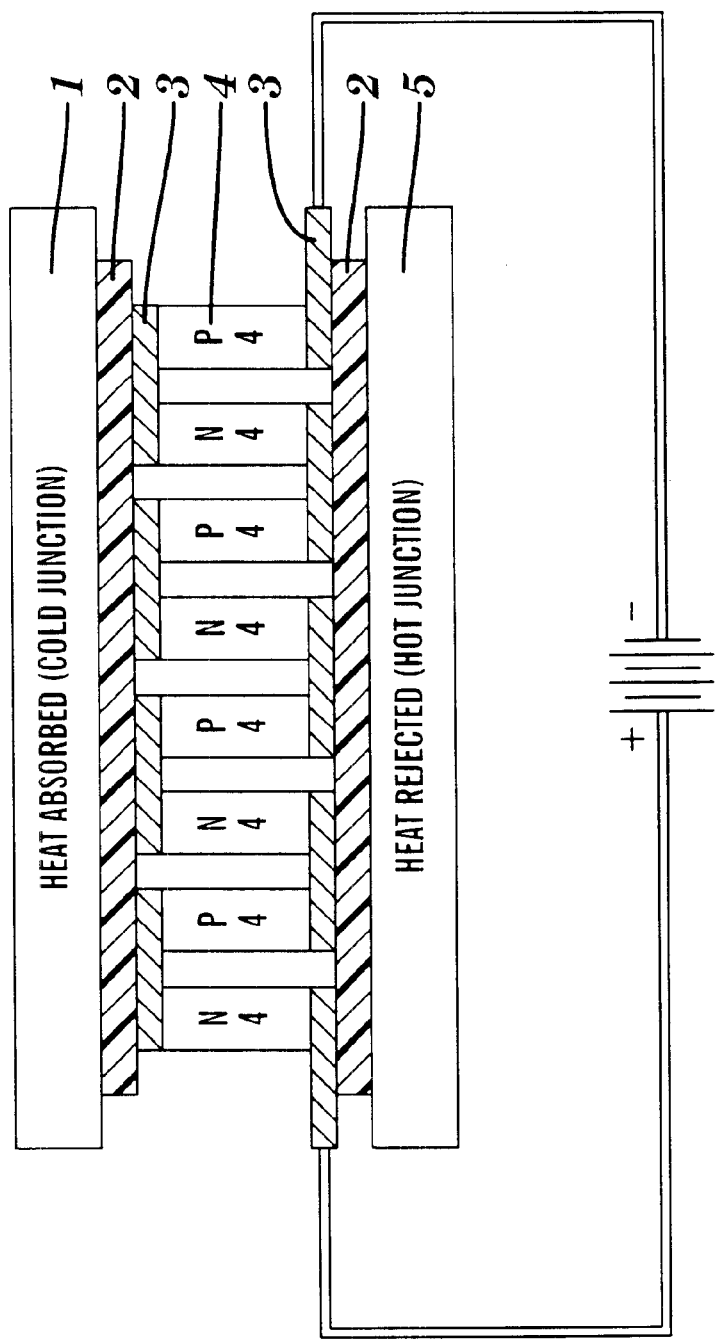
FIG. 3 shows a schematic representation of a typical thermoelectric thermopile module.

The contrast between adiabatic calorimetry and heat conduction calorimetry is illustrated in FIG. 1. For adiabatic calorimetry, the temperature (T) vs. time is measured in an adiabatic vessel of known heat capacity (C) to provide the heat (Q). For heat conduction calorimetry, the thermal power vs. time (t) is measured in a vessel in which the heat (Q) generated by the chemical process flows through a heat flow sensor. The basic equations for heat conduction calorimetry or "Calvet calorimetry" are shown in FIG. 2, where P is the thermal power in Watts, S is the thermopile sensitivity in volts/watt, U is the thermopile voltage in volts, and τ is the time constant of the calorimeter in seconds. At steady state, U=SP. The time constant is determined by C/G, where C is the heat capacity of the reaction vessel and G is the thermal conductance of the thermopile. The sensing element in a heat flow sensor, such as a heat conduction calorimeter, is typically a thermopile, or thermoelectric, module. Examples of these thermopile modules are manufactured by Melcor, Inc., of Trenton, N.J., and are widely used as thermoelectric heat pumps in computers and other electronics. FIG. 3 shows some design details of a typical thermoelectric thermopile, as, for example, those made by Melcor, Inc. The top layer 1 of the assembly is a cold junction where heat is absorbed. The electrical insulator layer 2 and electrical conductor layer 3 are on both sides of bismuth telluride elements 4 with "N" and "P" type properties. The bottom layer 5 of the assembly is a hot junction where heat is rejected. The elements are electrically connected in series through a direct current (dc) source and are thermally in parallel. In practical use, couples are combined in a module where they are connected electrically in series, and thermally in parallel. Normally a module is the smallest component commercially available. Modules are available in a great variety of sizes, shapes, operating currents, operating voltages, and ranges of heat pumping capacity.

Mass and Heat Flow Measurement Apparatus and System

Figure 4:
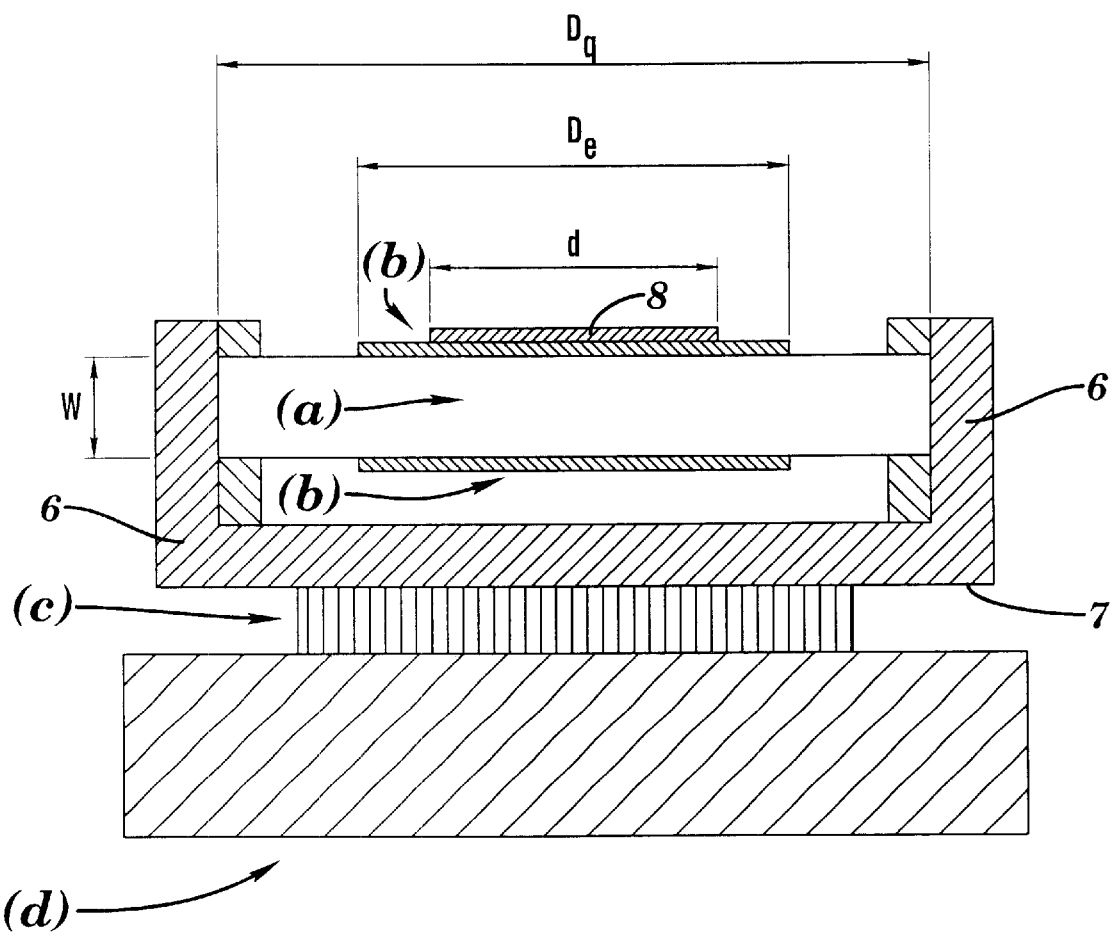
FIG. 4 shows a schematic representation of a quartz crystal microbalance and heat flow sensor combination device.

A schematic diagram of one aspect of the microresonator and heat flow sensor combination device is shown in FIG. 4. This sensor combination device is combined with at least one additional sensor combination device to provide the combined microresonator and heat flow sensor sample and reference devices in the novel apparatus and method of the present invention. As illustrated in FIG. 4, a circular disk, (a), of an AT-cut quartz crystal of diameter, $D_q$, and thickness, w, is mounted with its circumferential edge or perimeter in good thermal contact to a metallic cylinder 6 with a bottom plate 7. The disk has electrodes (b) of diameter, $D_e$, deposited on both faces. The bottom plate is in contact to a thermopile (c), which is in turn in contact to a heat sink (d), for example, the bottom of a can which is thermostated in a constant temperature bath. Thus, the heat flow sensor comprising the thermopile is coupled thermally to the microresonator, and the heat sink is coupled thermally to the heat flow sensor. On the top surface or first face of the quartz crystal oscillator with electrode is deposited a sample 8 in a circular area of diameter, d. It is this sample which will produce a heat flow rate, ϕ (watts), when, for example, subliming, adsorbing, desorbing, or reacting at a rate of dn/dt moles per second, where the symbol, $\Delta H_{sub}$, is used to represent the enthalpy change of any of the processes mentioned above and $\phi = \Delta H_{sub}$ dn/dt. For example, a typical sublimation enthalpy of 50 kJ mol$^{-1}$, combined with a heat flow rate of 100 nW typical of the baseline noise in a good heat conduction microcalorimeter, corresponds to a sublimation rate, dn/dt, of $5.0 \times 10^{-12}$ mole sec$^{-1}$. For a substance of molar mass of 200 g mol$^{-1}$, this corresponds to a mass loss of 1.0 ng sec$^{-1}$. The Nanowatt Amplifier available from Thermometric AB in Sweden, as described in *Thermometric Calorimeter News*, February 1997, page 3, with a noise level for an empty ampoule heat conduction calorimeter of 2 nW, will increase this sensitivity by a factor of 50, or to $1.0 \times 10^{-13}$ mole sec$^{-1}$ (20 pg sec$^{-1}$). The bottom surface or opposite face of the quartz crystal with electrodes is isolated from contacting the sample.

A key requirement in the microresonator and heat flow sensor combination device is to provide a path of high thermal conductivity from the piezoelectric crystal surface to the heat flow sensor. Otherwise, at high heat flow rates, the central portion of the piezoelectric crystal surface may heat up, thus producing temperature gradients within the crystal and accompanying shifts in resonant frequency. There must be good thermal contact between the piezoelectric crystal and the mounting of the thermally conductive material, so the details of mechanical support are important. In Chapter 10 of the above-mentioned reference by Bottom, it is shown that the quartz between the two circular deposited electrodes is the region undergoing transverse shear waves, and that the surrounding bare quartz annulus serves to damp higher acoustic modes. To the first approximation, the annulus functions as an acoustical node. It is therefore available to mount the crystal and make a path of high thermal conductivity between the piezoelectric substrate and the heat flow sensor without affecting the high quality factor, Q, of acoustical vibrations at resonance. FIG. 4 shows one possible mounting arrangement of the microresonator and heat flow sensor combination device. The heat conductive material providing the high thermal conductivity between the piezoelectric substrate and the heat flow sensor is not in contact with the acoustically active region undergoing transverse shear waves, including the acoustically active region on the opposite face of the piezoelectric crystal.

It is possible to estimate the temperature gradient in the quartz between the two electrodes under operating conditions for a microresonator comprising a quartz crystal. The radial temperature distribution, T(r), in a disk of diameter, $D_e$, and thickness, c, connected to a heat sink of temperature, $T_0$, at its edge and uniformly heated on its surface with an input power per unit area, P, has been derived by Ginnings et al., in "Principles of Calorimetric Design" in *Experimental Thermodynamics: Calorimetry of Non-Reacting Systems*, Vol. 1, edited by McCullough et al., Butterworth, London, 1968, as follows:

$$T(r) - T_0 \approx P/4\lambda e \, [D_e^2/4 - r^2]$$

where λ is the thermal conductivity of the disk material. Thermal conductivity in quartz is anisotropic. For heat flow along the C-axis (the optical axis), λ=11.1 W K$^{-1}$ m$^{-1}$, whereas for a perpendicular axis, λ=5.88 W K$^{-1}$ m$^{-1}$. To estimate temperature gradients, we take the mean, λ=8.5 W K$^{-1}$ m$^{-1}$, and use the dimensions given above ($D_e$=0.0025 m, e=0.000154 m, or electrode area=$4.91 \times 10^{-6}$ m$^2$). Assuming a heat flow of 100 μW, or 10$^{-3}$ times the noise level of the microcalorimeter, the temperature difference between the center of the disk and the edge of the electrode (r=$D_e$) is only $6 \times 10^{-3}$ K, independent of disk diameter. This is much too small to create spurious effects due to the temperature dependence of the quartz. Thus, for example, quartz is an adequate thermal conductor to function in the microresonator and heat flow sensor combination of the present invention.

For the embodiment shown in FIG. 4, the "reaction vessel" of the microresonator and heat flow sensor of this invention has a small heat capacity and thus a short time constant, as, for example, described in *J. Biochemical and Biophysical Methods*, Vol. 28, pages 85–100 (1994), by Backman et al. This short time constant may perhaps be as short as a few seconds. This makes less demands on the long-term stability of both the microresonator and the heat flow sensor and the temperature stability of the heat sink. The short time constant will also be useful in following the kinetics of adsorption or desorption of materials. The operating frequency of the microresonator should be high enough to assure good counting statistics in the frequency measurement, but high frequencies imply thin quartz crystals and a corresponding fragility and a decrease in thermal conductivity. The width, w, of the microresonator is a design parameter to be determined by optimizing these conflicting requirements.

As shown in FIG. 4, one embodiment of the microresonator and heat flow sensor combination device is a single device incorporating one microresonator, such as a quartz crystal microbalance, and one heat flow sensor comprising a thermopile for mass and heat flow measurements.

Figure 5:
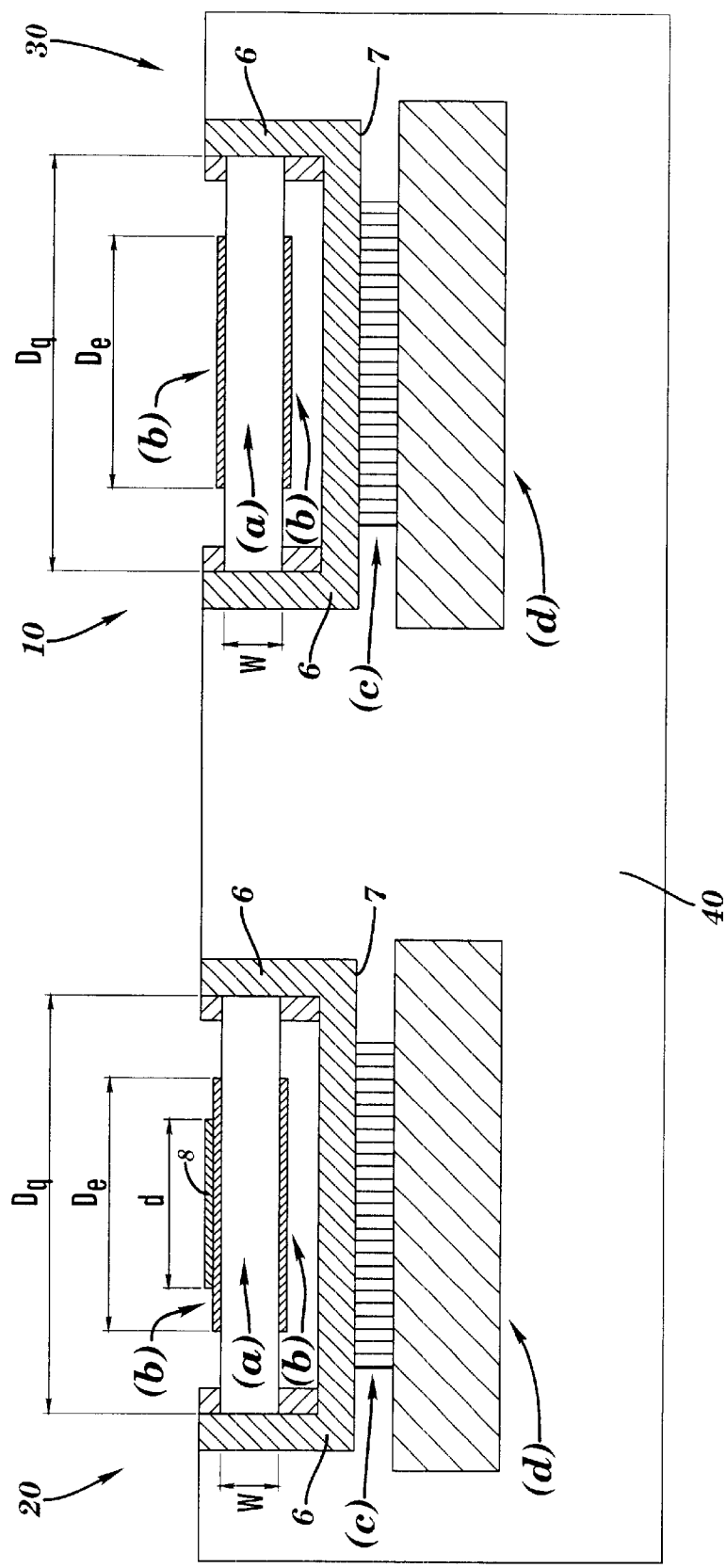
FIG. 5 shows a schematic representation of one embodiment of the multiple quartz crystal microbalance and heat flow sensor combination devices in accordance with one embodiment of the present invention.

FIG. 5 shows one embodiment of the combined microresonator and heat flow sensor sample and reference devices of the present invention. The apparatus 30 (not to scale) includes two microresonator and heat flow sensor combination devices, one serving as a reference sensor 10 and one as a sample sensor 20 on which the sample (8) is placed. Each sensor combination device in FIG. 5 has the elements as illustrated and labeled for the single combination device shown in FIG. 4 and is housed in a chamber 40 containing electronics and other components. The metallic analysis 6, which acts as a heat conductive material coupling the heat flow sensor to the microresonator, may be in a variety of designs, such as D-shaped half cylinders, and may be made of a variety of good thermal conducters such as brass, and copper.

Figure 6:
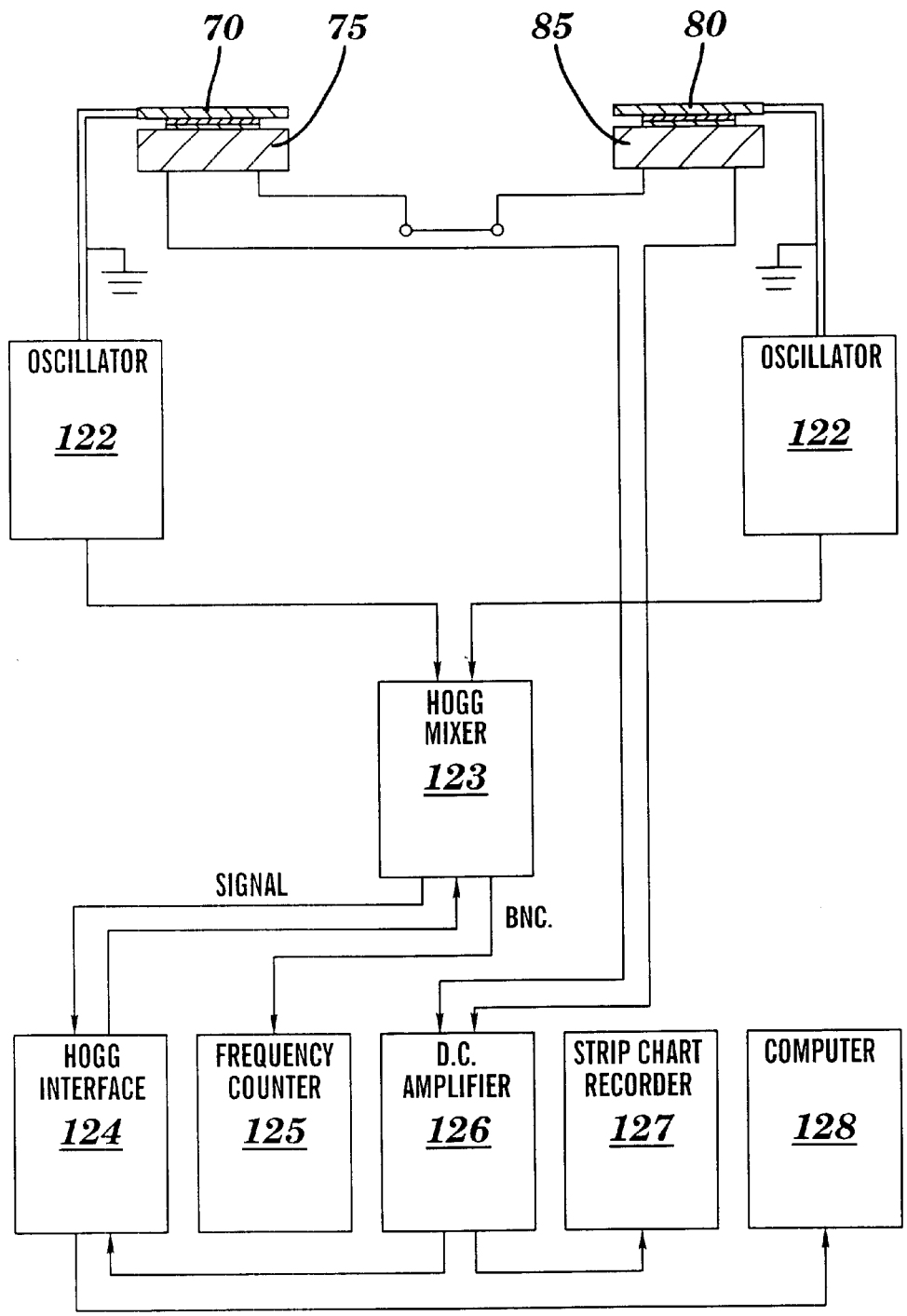
FIG. 6 shows a block diagram schematic of the electronics of the devices shown in FIG. 5.

FIG. 6 shows a schematic diagram of the combined microresonator and heat flow sensor sample and reference device electronics for the apparatus of FIG. 5. The sample quartz crystal microbalance 70, reference quartz crystal microbalance 80, sample thermopile 75, and reference thermopile 85 are connected electronically to provide the measurement signals through the use of an oscillator 122, a signal mixer 123, an interface 124, a frequency counter 125, a dc amplifier 126, a strip chart recorder 127, and a computer 128. The voltage from the thermopile sensors is the difference in voltage between sample and reference heat flow sensors, and the frequency from the mass measurement channel is the difference in frequency between the two microresonators.

Figure 7:
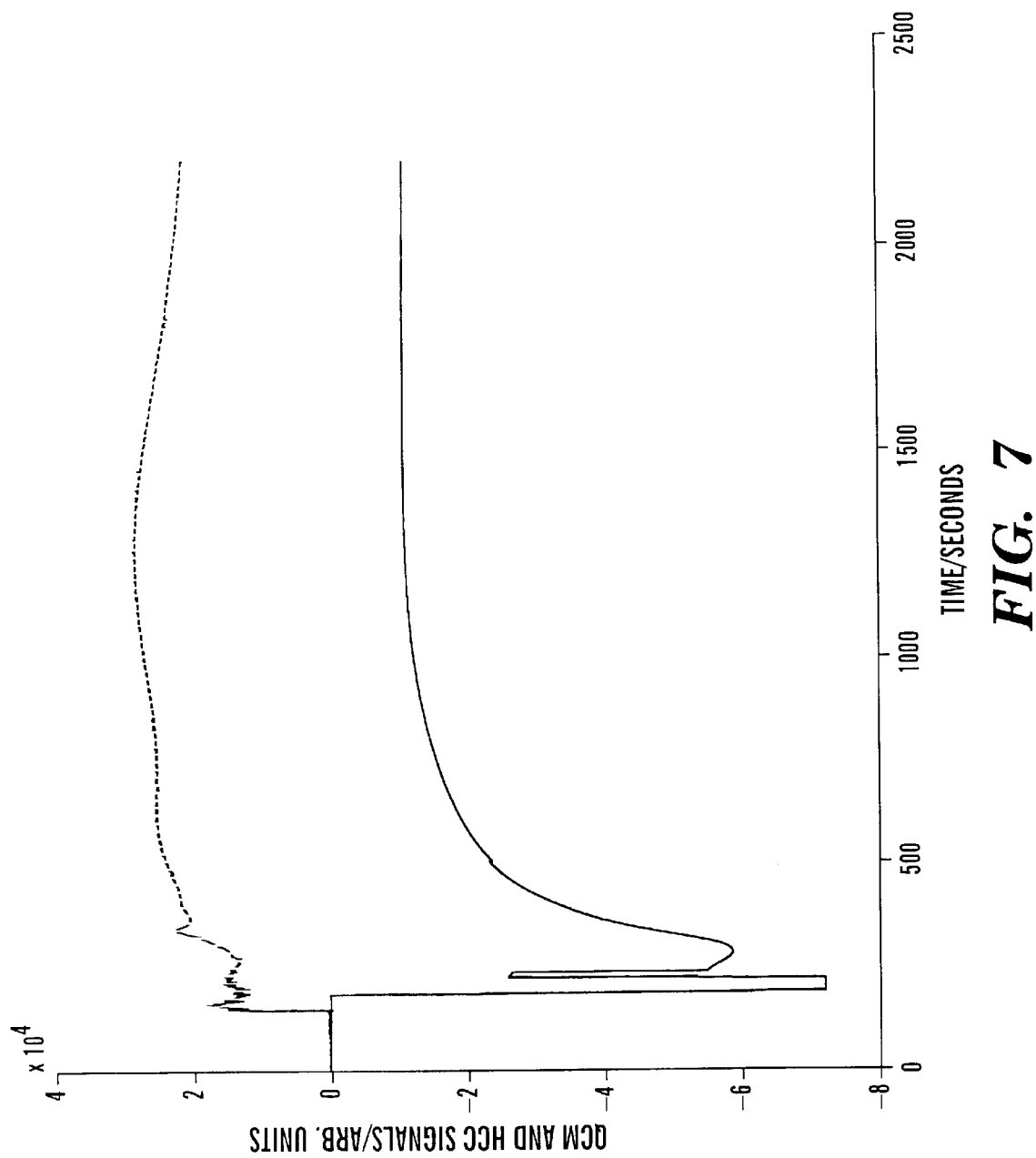
FIG. 7 shows a graphical representation of the response of the devices of FIG. upon deposition of a drop of heptane.

Preliminary experiments showed that the combined microresonator and heat flow sensor apparatus, as illustrated in one embodiment in FIGS. 5 and 6, has a high sensitivity in both mass measurement and heat flow measurement. For example, FIG. 7 shows the response of both channels when a 5 microliter drop of decane was deposited on the sample quartz crystal microbalance. The dashed line is the response of the quartz crystal microbalance channel in Hz, and the continuous line is the response of the heat flow sensor whose signal was about 1 milliwatt full scale.

Figure 8:
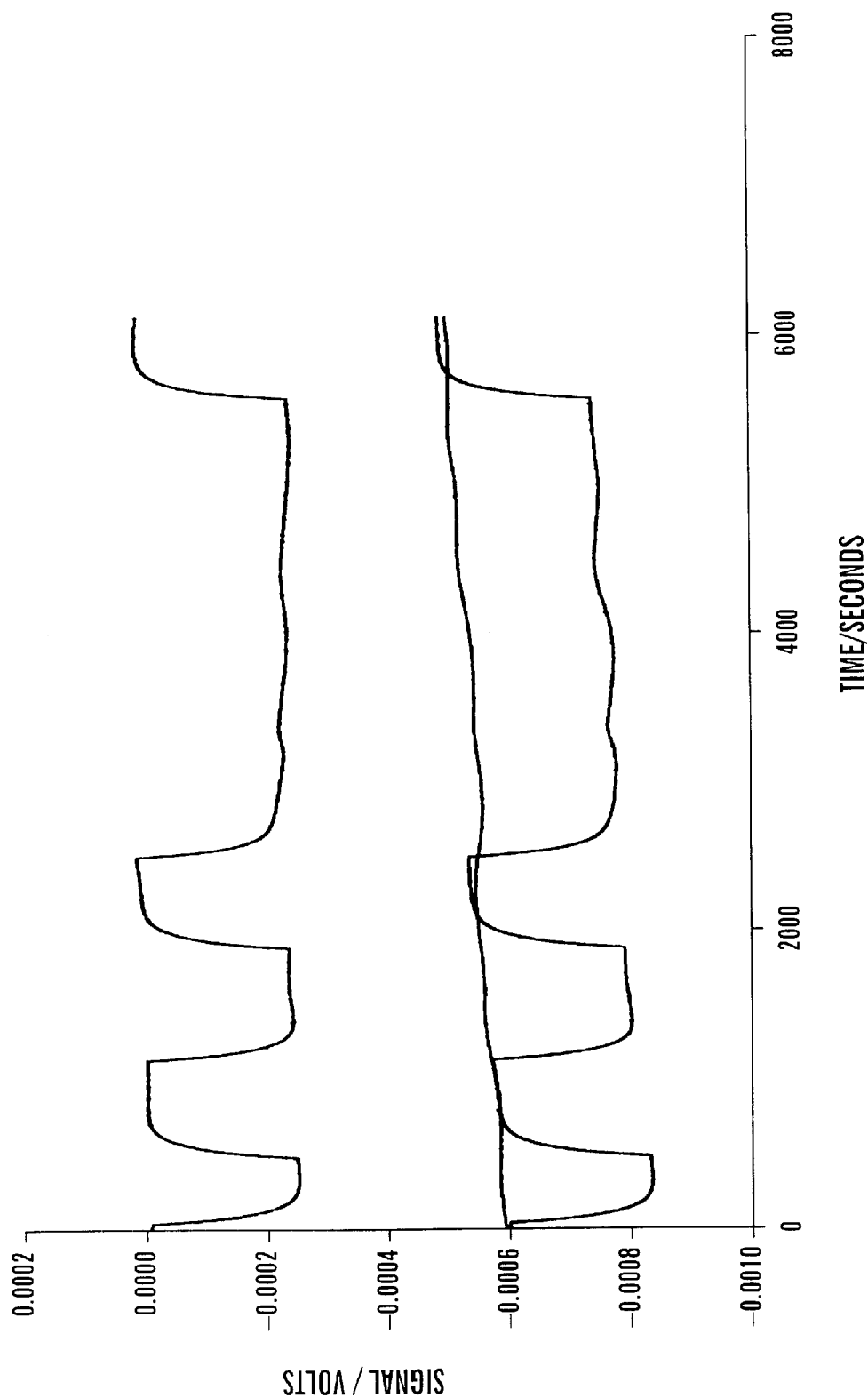
FIG. 8 shows a graphical representation of the calibration of the devices of FIG. 5 utilizing a helium-neon (He—Ne) laser.

Calibration of the thermopile of the heat flow sensor is accomplished, for example, by shining a 0.95 milliwatt He—Ne laser onto each microresonator of the microresonator and heat flow sensor combination and measuring the resulting heat flow sensor voltage. FIG. 8 shows an example of this calibration.

Figure 9:
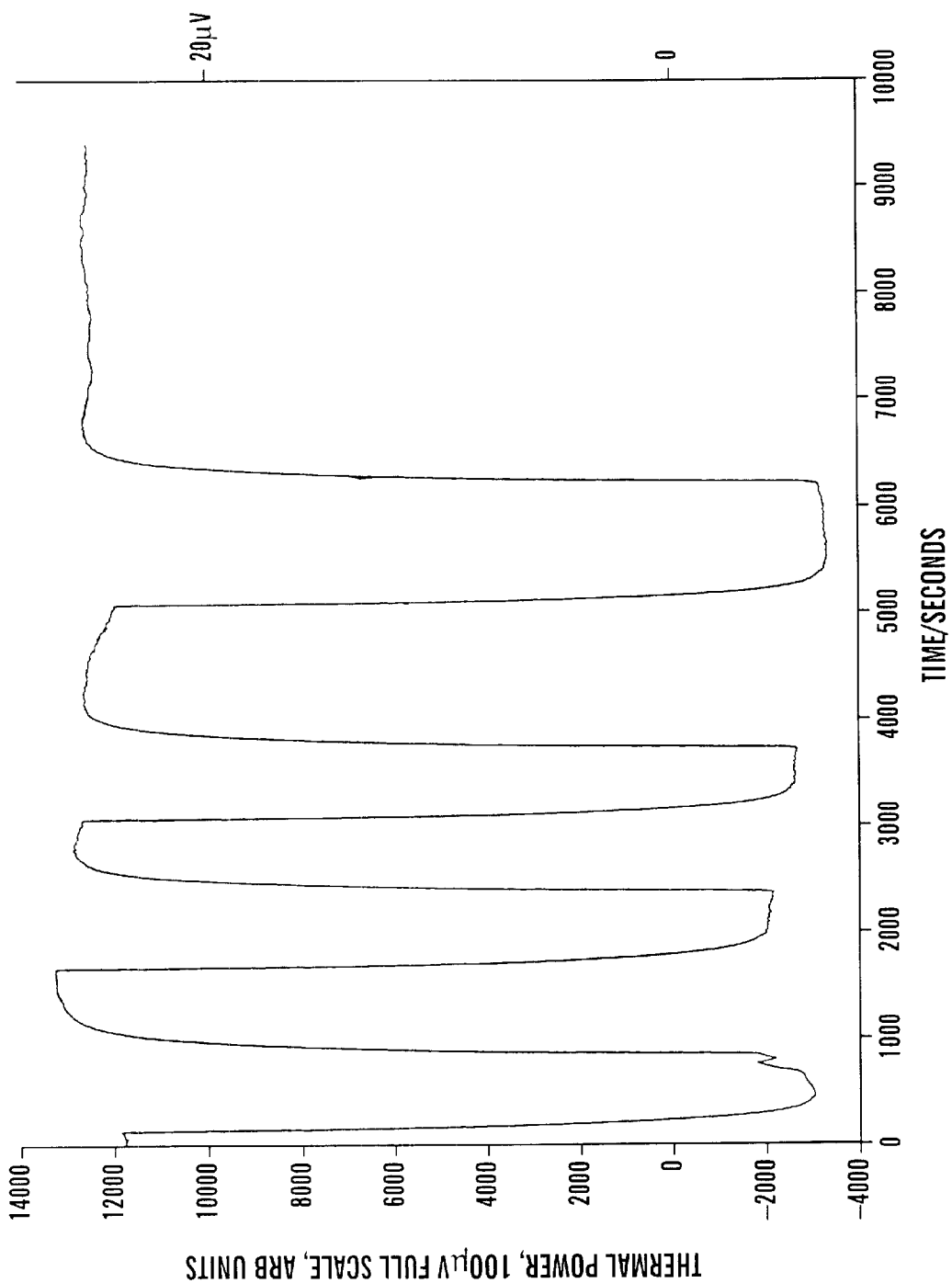
FIG. 9 shows a graphical representation of the heat generated by the devices of FIG. 5 upon the application of 5.0 MHz rf power.

When 5.0 MHz of radio-frequency (rf) power was supplied to the piezoelectric quartz crystal of the quartz crystal microbalance, the heat generated (about 115 microwatts) could be readily detected by the heat flow sensor. FIG. 9 shows this effect.

The expected detection limits of the heat flow and mass change measurements of the microresonator and heat flow sensor combination may be estimated. For a microresonator, such as a quartz crystal microbalance, the frequency shift, $\delta\upsilon$, is related to the mass change per unit area, $\delta m$, deposited on the microresonator surface by the Sauerbrey equation, which for the embodiment of a quartz crystal microbalance shown in FIG. 4, can be expressed as:

$$\delta\upsilon = -57\ \delta m$$

where the frequency shift is in Hz and the mass change is in micrograms/cm$^2$. Since the observed short-term stability of the quartz crystal microbalance is about ±1 Hz in its present configuration, the mass detection limit is presently about 18 ng/cm$^2$. With better counting electronics, this limit could be reduced by at least an order of magnitude. The sensitivity of the heat flow sensor is about 0.3 V/W, so the observed rms noise in the heat flow sensor output channel of ±1 microvolt corresponds to a heat conduction detection limit of 3 microwatts.

One aspect of the present invention pertains to a mass and heat flow measurement apparatus comprising (i) a sample sensor comprising a first microresonator, a first heat flow sensor, and a heat sink coupled thermally to the first heat flow sensor, wherein the first heat flow sensor is thermally coupled to the first microresonator; and further wherein the first microresonator is capable of measuring the mass of a sample in contact with the first microresonator, and the first heat flow sensor is capable of measuring the flow of heat from the sample to the heat sink; (ii) a reference sensor comprising a second microresonator, a second heat flow sensor coupled thermally to the second microresonator, and a heat sink coupled thermally to the second heat flow sensor; and, (iii) a chamber housing the sample and reference sensors, wherein the reference sensor is isolated from the sample; and further wherein the second microresonator is capable of measuring a reference signal relating to mass at a surface of the second microresonator, and the second heat flow sensor is capable of measuring a reference signal relating to the flow of heat from the surface of the second microresonator to the heat sink coupled thermally to the second heat flow sensor. In one embodiment, the first microresonator comprises a piezoelectric substrate having a perimeter, a first face for directly contacting the sample, and a second opposite face isolated from contacting the sample; and further wherein the second microresonator comprises a piezoelectric substrate having a perimeter, a first face, and a second opposite face, the piezoelectric substrates of the first and second microresonators having a resonant frequency and capable of providing a measurement signal based on the resonant frequency. In one embodiment, the sample is a solid sample.

A wide variety of microresonators may be utilized in the mass and heat flow measurement apparatus and systems of the present invention as, for example, the microresonators described in the afore-mentioned references by Grate et al., Alder et al., McCullen, and Lu et al. Suitable microresonators for the apparatus of this invention include, but are not limited to, bulk acoustic wave sensors, quartz crystal microbalances, surface acoustic wave sensors, flexural plate wave sensors, and acoustic plate mode sensors. In a preferred embodiment, the first and second microresonators of the apparatus of the present invention are quartz crystal microbalances. In one embodiment, the first microresonator comprises a surface coating with an affinity for at least one component of the sample. In one embodiment, the second microresonator comprises a surface coating with an affinity for at least one component of the sample.

A wide variety of heat flow sensors may be utilized in the mass and heat flow apparatus and systems of the present invention, such as, for example, the isothermal heat conduction calorimeters described in *Chemical Society Reviews*, Volume 1997, pages 79–86 (1997) by Wadso and references therein. In one embodiment, the first and second heat flow sensors of the apparatus of this invention comprise a thermopile.

Another aspect of the present invention pertains to a mass and heat flow measurement system comprising (i) at least one mass and heat flow measurement sample sensor comprising a microresonator, a heat flow sensor coupled thermally to the microresonator, and a heat sink coupled thermally to the heat flow sensor, wherein the microresonator generates data relating to the changes in mass on a surface of the microresonator arising from contacting the microresonator with a sample; and further wherein the heat flow sensor generates data relating to the changes in flow of heat from the sample to the heat sink from contacting the microresonator with the sample; (ii) at least one mass and heat flow measurement reference sensor comprising a reference microresonator, a reference heat flow sensor coupled thermally to the reference microresonator, and a heat sink coupled thermally to the reference heat flow sensor, wherein the microresonator of the reference sensor is not in contact with the sample; and further wherein the reference microresonator generates data relating to the changes in mass on a surface of the reference microresonator, and the reference heat flow sensor generates data relating to the changes in flow of heat from the surface of the reference microresonator to the heat sink coupled thermally to the reference heat flow sensor; and, (iii) a measurement instrument capable of correlating data from the sample and reference sensors so as to provide measurement of the mass of the sample and the flow of heat from the sample to the heat sink coupled thermally to the heat flow sensor of the sample sensor. In one embodiment of the system of this invention, the microresonator of the sample sensor comprises a piezoelectric substrate having a perimeter, a first face for directly contacting a sample, and a second opposite face isolated from contacting the sample; and further wherein the reference microresonator comprises a piezoelectric substrate having a perimeter, a first face, and a second opposite face, the piezoelectric substrates of the microresonator of the sample sensor and the reference microresonator having a resonant frequency and capable of providing a measurement signal based on the resonant frequency. In one embodiment, the sample is a solid sample.

Suitable microresonators for the sample sensor and suitable reference microresonators for the system of the present invention include, but are not limited to, bulk acoustic wave sensors, quartz crystal microbalances, surface acoustic wave sensors, flexural plate wave sensors, and acoustic plate mode sensors. In a preferred embodiment, the microresonator of the sample sensor and the reference microresonator are quartz crystal microbalances. In one embodiment, the microresonator of the sample sensor comprises a surface coating with an affinity for at least one component of the sample. In one embodiment, the reference microresonator comprises a surface coating with an affinity for at least one component of the sample.

In one embodiment, the heat flow sensor of the sample sensor and the reference heat flow sensor of the system of the present invention comprise a thermopile.

To facilitate the introduction of both liquid and gaseous samples to either the sample or reference microresonator and heat flow sensor combination device, KEL-F inserts which screw into the top of the aluminum sample and reference chambers were designed and constructed. In one embodiment, each insert directs three TEFLON (a trademark for polytetrafluoroethylene polymer available from DuPont Corporation, Wilmington, Del.) tubes of 0.6 mm i.d. into the region above the microresonator surface. For example, one tube is used to transport liquids to the surface of the microresonator, and the other two are used as gas inflow and outflow leads.

Figure 10:
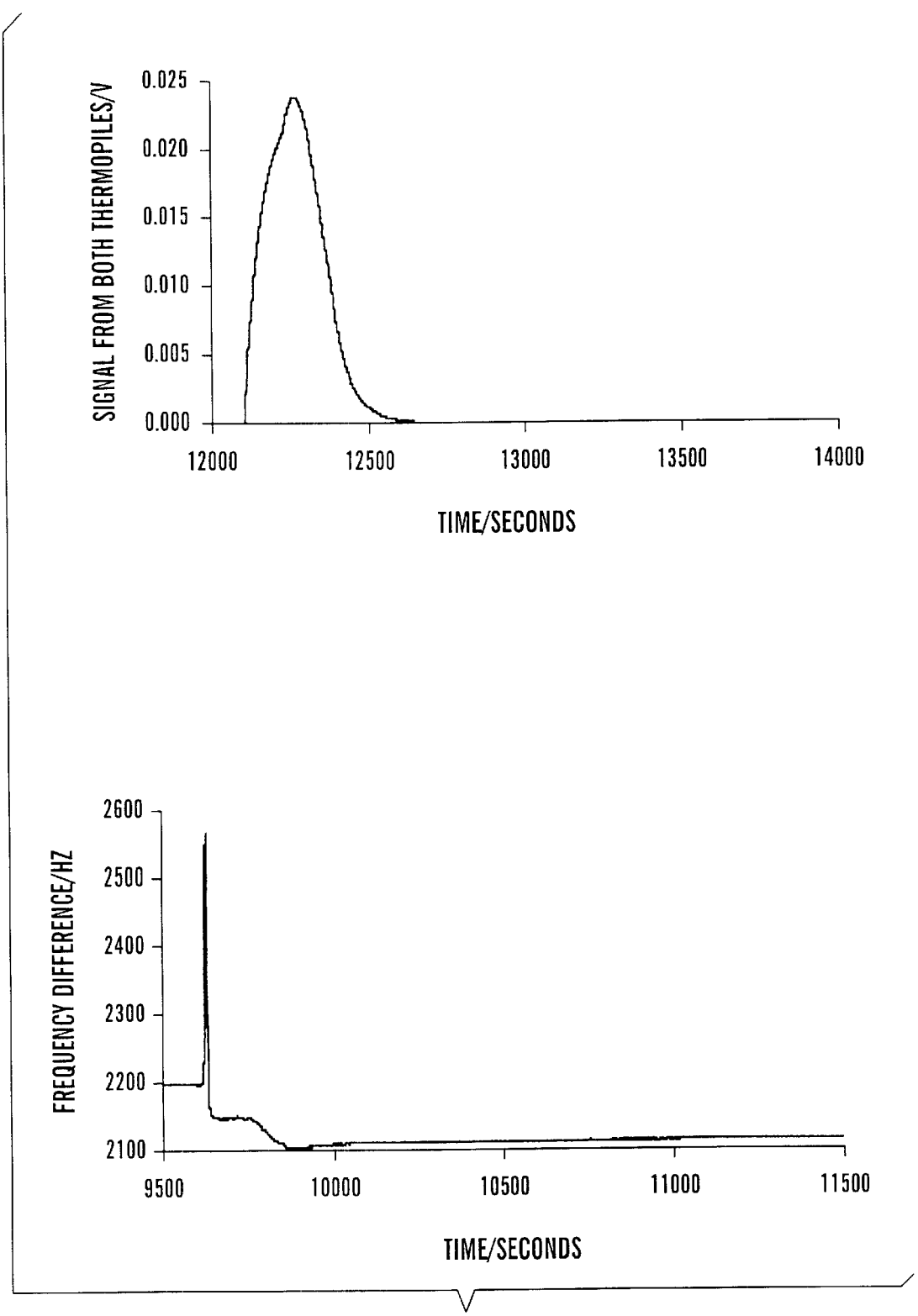
FIG. 10 shows a graphical representation of the heat flow and mass change signals of the devices shown in FIG. 5 upon the deposition of 20 mg of hexane on the surface of the quartz crystal microbalance in the left quartz crystal microbalance and heat flow sensor combination device.
Figure 11:
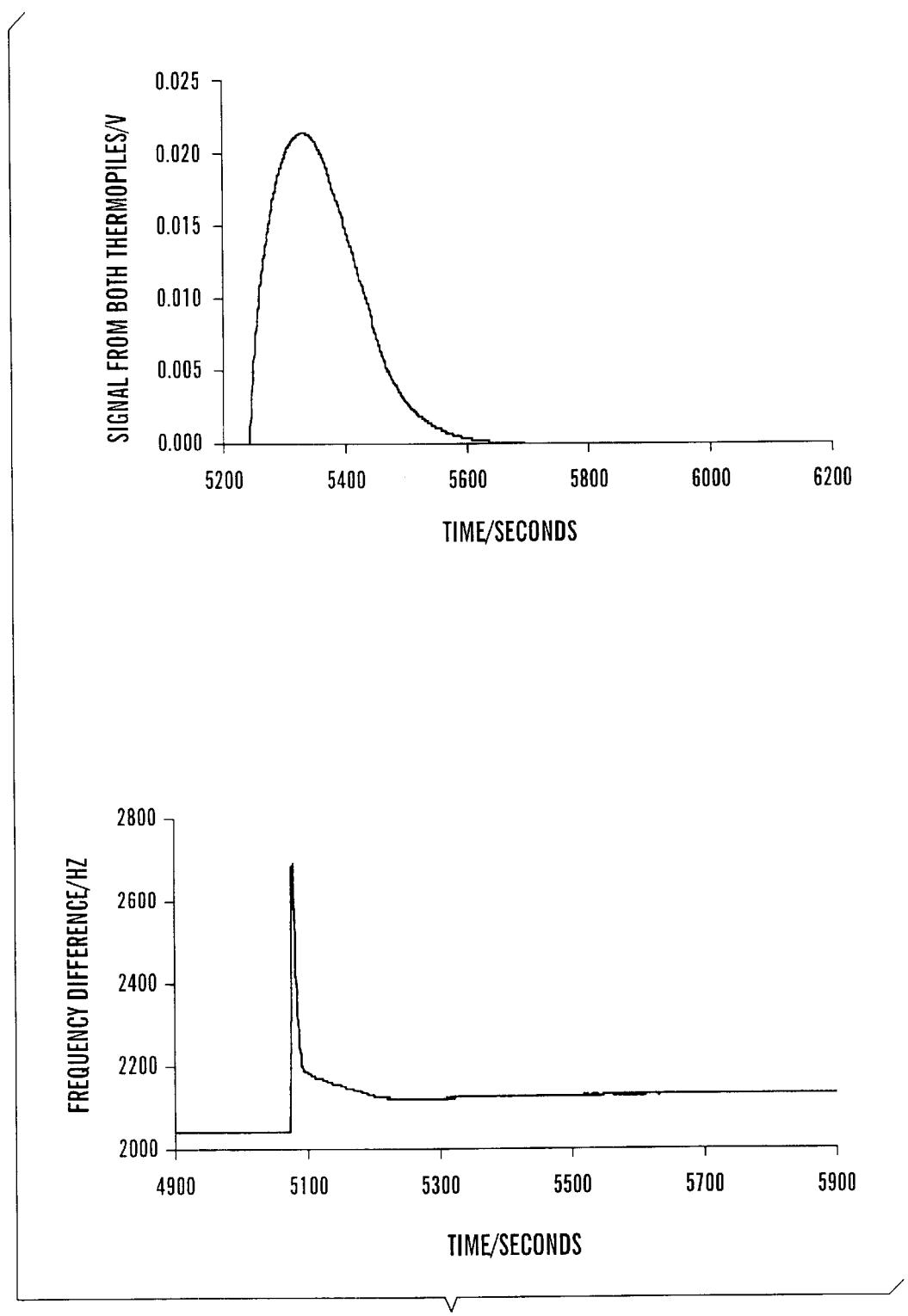
FIG. 11 shows a graphical representation of the heat flow and mass change signals of the devices shown in FIG. 5 upon the deposition of 20 mg of hexane on the surface of the quartz crystal microbalance in the right quartz crystal microbalance and heat flow sensor combination device.

FIGS. 10 and 11 show the mass and heat flow changes when 1 drop of hexane (20 mg) is deposited on the left and right quartz crystal microbalance and heat flow sensor combination devices, respectively. On the right quartz crystal microbalance and heat flow sensor combination device, the strong endothermic signal from the heat flow sensor integrates to a heat of 8 J absorbed by the evaporating hexane. The corresponding mass change cannot be detected while the quartz crystal microbalance surface is covered with liquid, because of the well-known inability of quartz crystal microbalances to measure accurately the mass of films with low viscoelasticities. However, the shift of the quartz crystal microbalance baseline (from before to after liquid deposition and evaporation) indicates that a residual deposit has been left on the approximately 1 $cm^2$ quartz crystal microbalance surface of 20 to 30 micrograms, or about 0.1% of the deposited hexane mass. Since no attempt was made to purify the hexane or to eliminate its contact with soluble organic impurities, such a shift is reasonable. It should be noted that the frequency shift is of opposite sign for the left and right quartz crystal microbalances. This is because the rf electronics detects the difference frequency between the two quartz crystal microbalances. The left quartz crystal microbalance oscillates at $5.0002 \times 10^6$ Hz and the right quartz crystal microbalance oscillates at $5.000 \times 10^6$ Hz, and the difference signal of about 2000 Hz is measured. When a deposit is placed on the left quartz crystal microbalance, its frequency decreases and the difference signal decreases. When a deposit is placed on the right quartz crystal microbalance, its frequency decreases and the difference signal increases.

Figure 12:
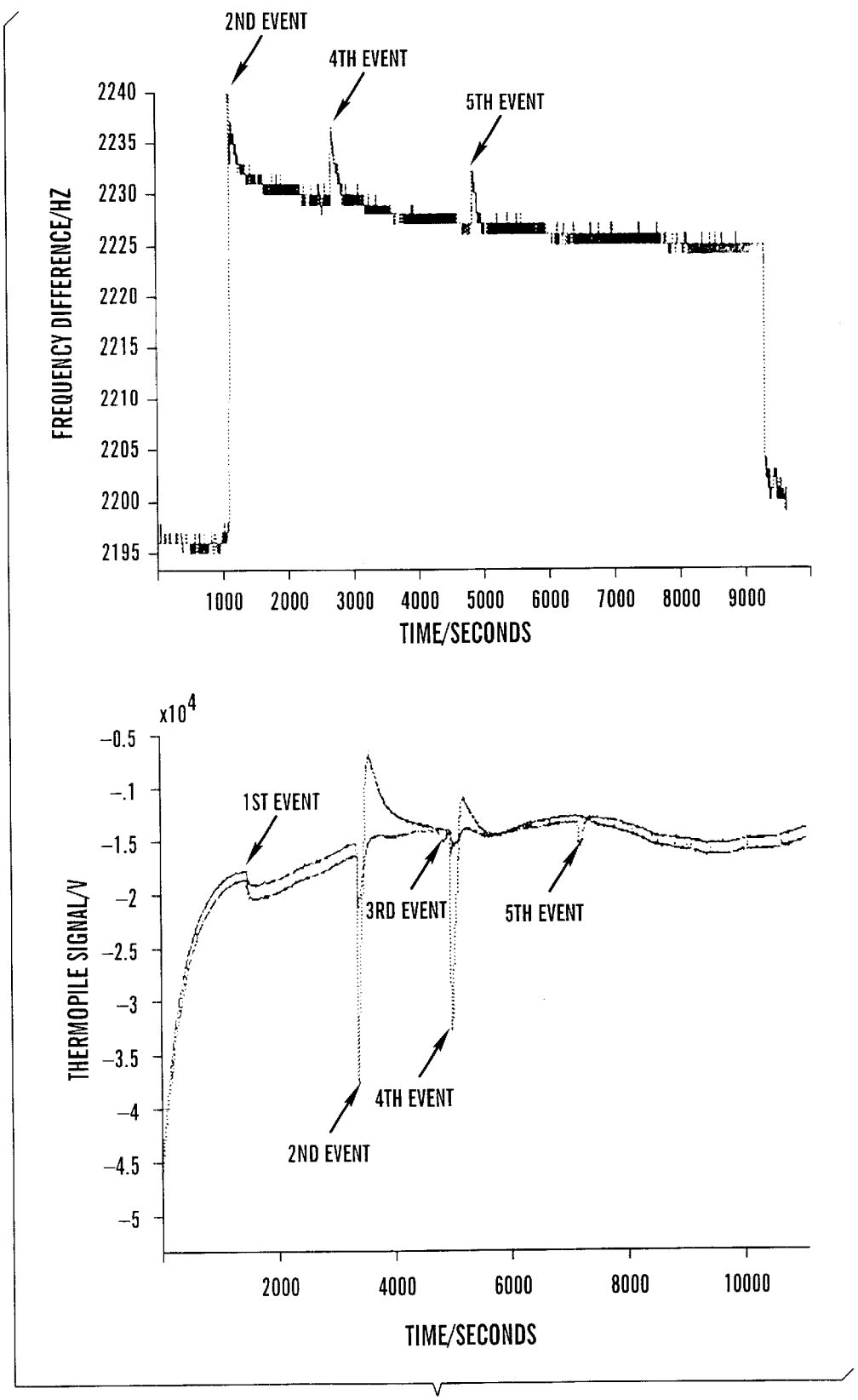
FIG. 12 shows a graphical representation of a quartz crystal microbalance output upon the introduction of organic vapors.

Since the deposition of organic liquids on the quartz crystal microbalance, even in small amounts, gave enormous heat flow sensor signals and uninterpretable quartz crystal microbalance signals, it was decided to study the response of the gold surface of the quartz crystal microbalance to the introduction of organic vapors. The hope was that these vapors would adsorb exothermically on the gold, thereby producing a corresponding mass increase. FIG. 12 shows experiments in which the top trace is the quartz crystal microbalance signal, and the bottom traces are the right and left heat flow sensor signals. At the first event, when the rf power to the two quartz crystal microbalances was turned on, both heat flow sensors responded with small exothermic signals, as expected. When the nitrogen gas was turned on and a small aliquot of methanol vapor was introduced into the flowing steam by allowing a 10 microliter drop of methanol to evaporate in a closed glass vial in series with the nitrogen gas flow, a prompt exothermic signal on the left heat flow sensor was observed, accompanied by a positive quartz crystal microbalance signal for the left quartz crystal microbalance to which the methanol vapor was introduced (the second event). After the aliquot of methanol had flushed through the sample chamber and was replaced by pure flowing nitrogen gas, the methanol adsorbed on the quartz crystal microbalance desorbed, and the heat flow sensor exhibited a corresponding slow endothermic signal while the quartz crystal microbalance signal returned to its value before the introduction of methanol. The same event was repeated in the fourth event, with similar signals being observed. For some reason as yet not understood, injection of a corresponding amount of methanol vapor on the right, or reference, quartz crystal microbalance and heat flow sensor combination device in the third event did not produce as large a signal. This could be due to differences in flow and a possible leak on the right hand side. In the fifth event, 10 microliters of hexane replaced the 10 microliters of methanol in a repeat of the second and fourth events and gave a slight exothermic signal in the left heat flow sensor, accompanied by a positive quartz crystal microbalance signal from the left quartz crystal microbalance.

Figure 13:
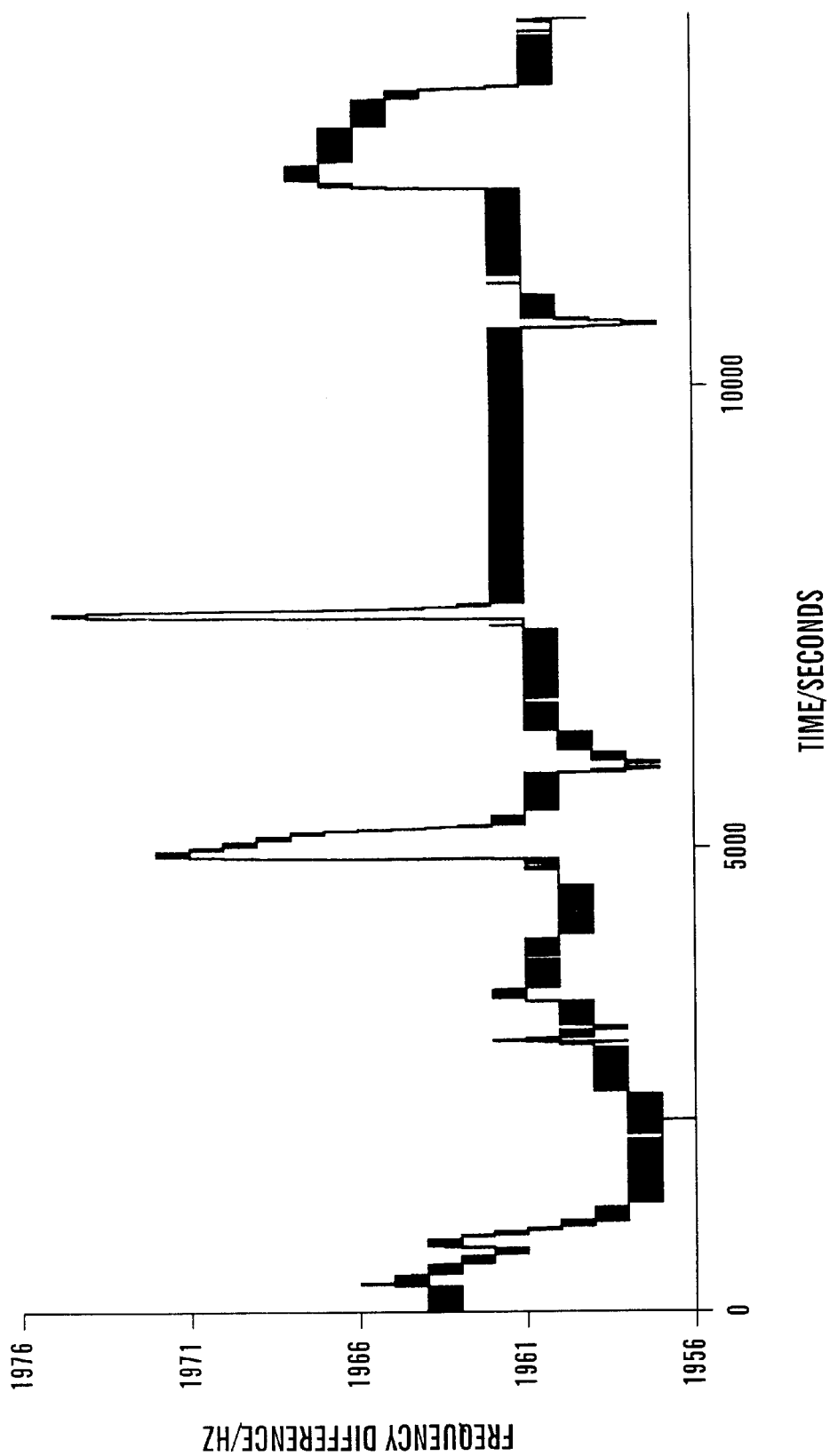
FIG. 13 shows diagrammatic representations of traces from the quartz crystal microbalance in the devices of FIG. 5 in response to the deposition of several organic vapors on the surface of one of the quartz crystal microbalances.
Figure 14:
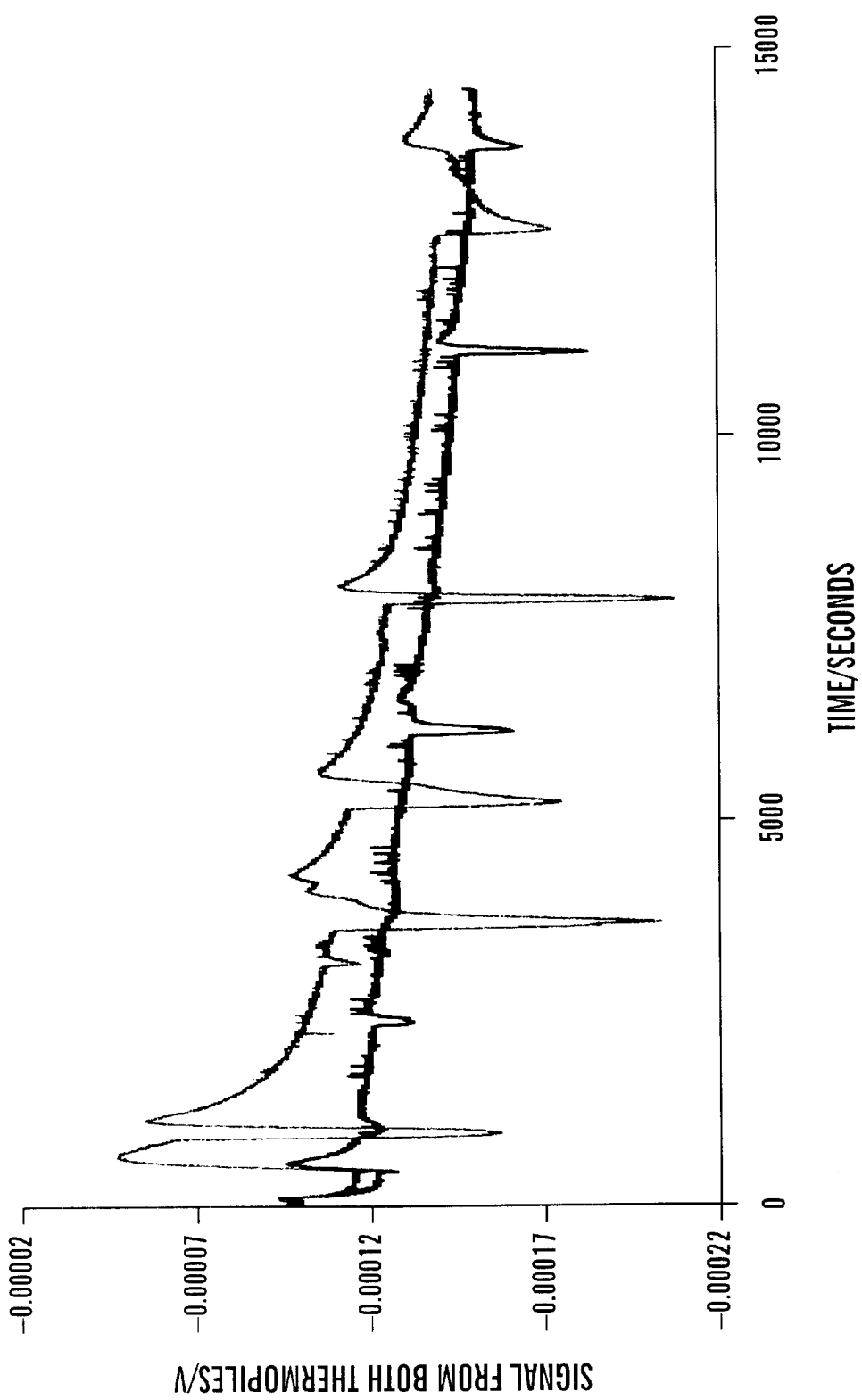
FIG. 14 shows diagrammatic representations of traces from both heat flow sensors in the devices of FIG. 5 in response to the deposition of several organic vapors on the surface of one of the quartz crystal microbalances.
Figure 15:
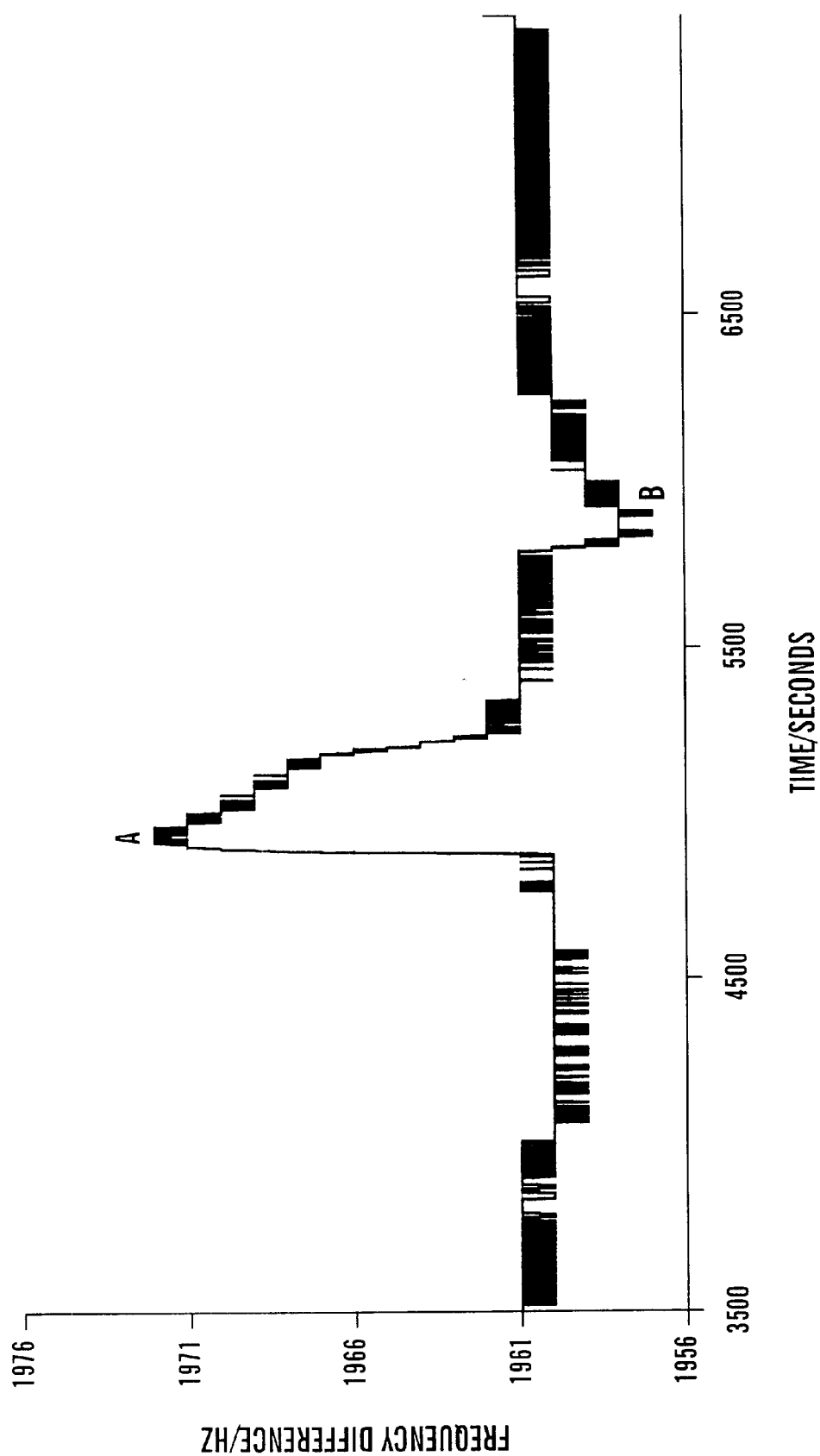
FIG. 15 shows diagrammatic representations for the quartz crystal microbalances in the devices of FIG. 5 in response to the deposition of toluene vapor on the surface of one of the quartz crystal microbalances.
Figure 16:
FIG. 16 shows diagrammatic representations for the heat flow sensors in the devices of FIG. 5 in response to the deposition of toluene vapor on the surface of one of the quartz crystal microbalances.
Figure 17:
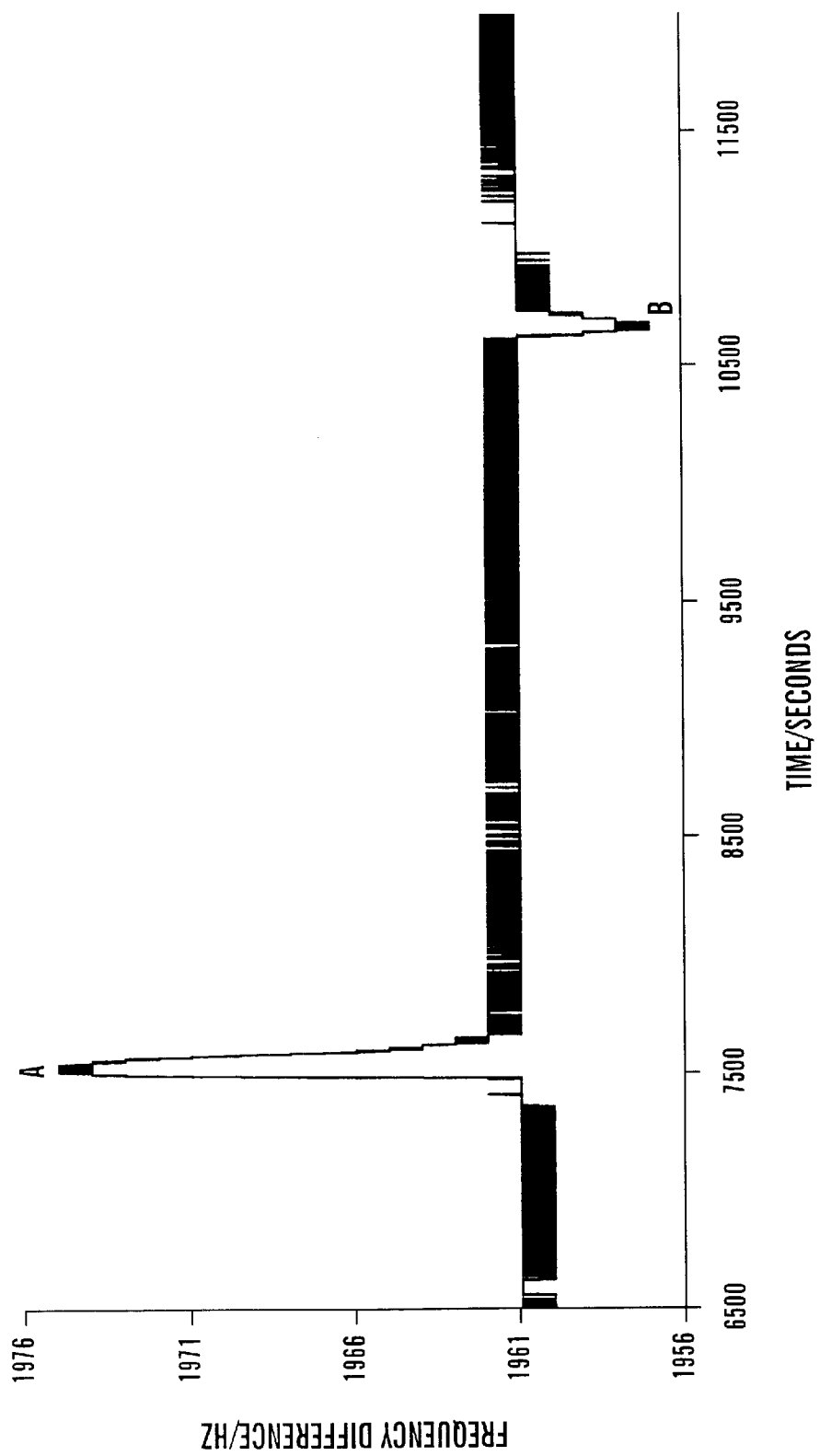
FIG. 17 shows diagrammatic representations for the quartz crystal microbalances in the devices of FIG. 5 in response to the deposition of chloroform vapor on the surface of one of the quartz crystal microbalances.
Figure 18:
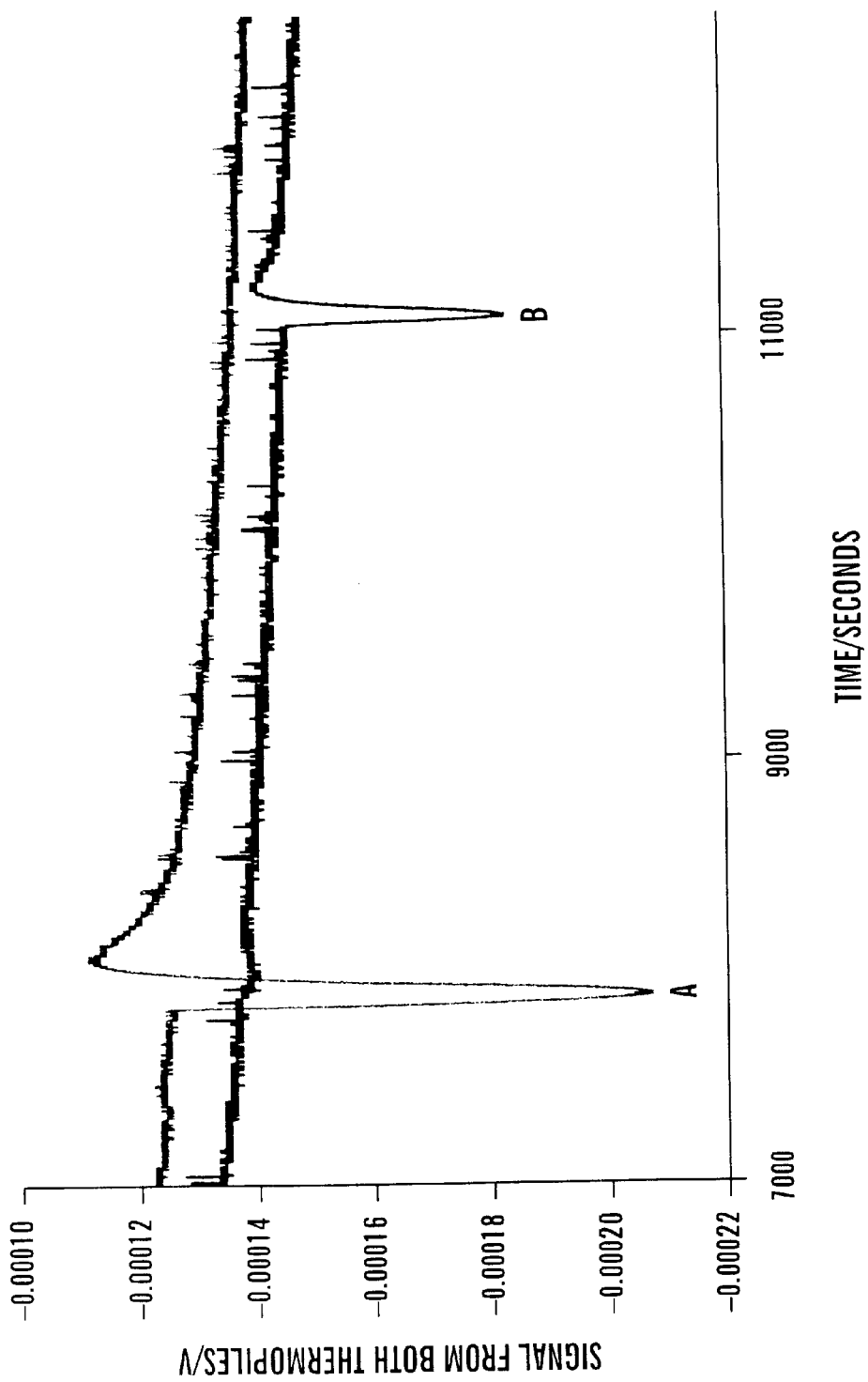
FIG. 18 shows diagrammatic representations for the heat flow sensors in the devices of FIG. 5 in response to the deposition of chloroform vapor on the surface of one of the quartz crystal microbalances.
Figure 19:
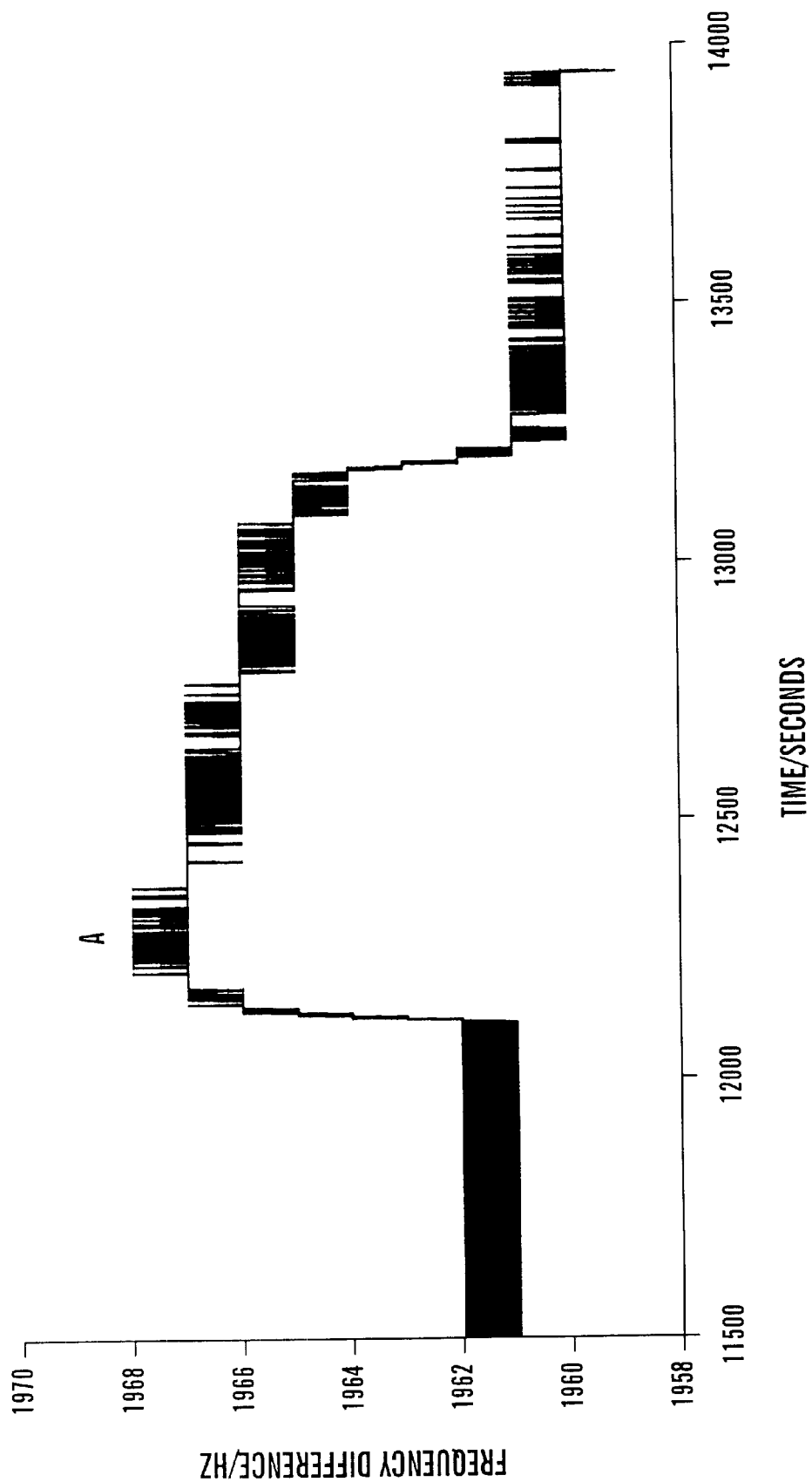
FIG. 19 shows diagrammatic representations for the quartz crystal microbalances in the devices of FIG. 5 in response to the deposition of n-butanol vapor on the surface of one of the quartz crystal microbalances.
Figure 20:
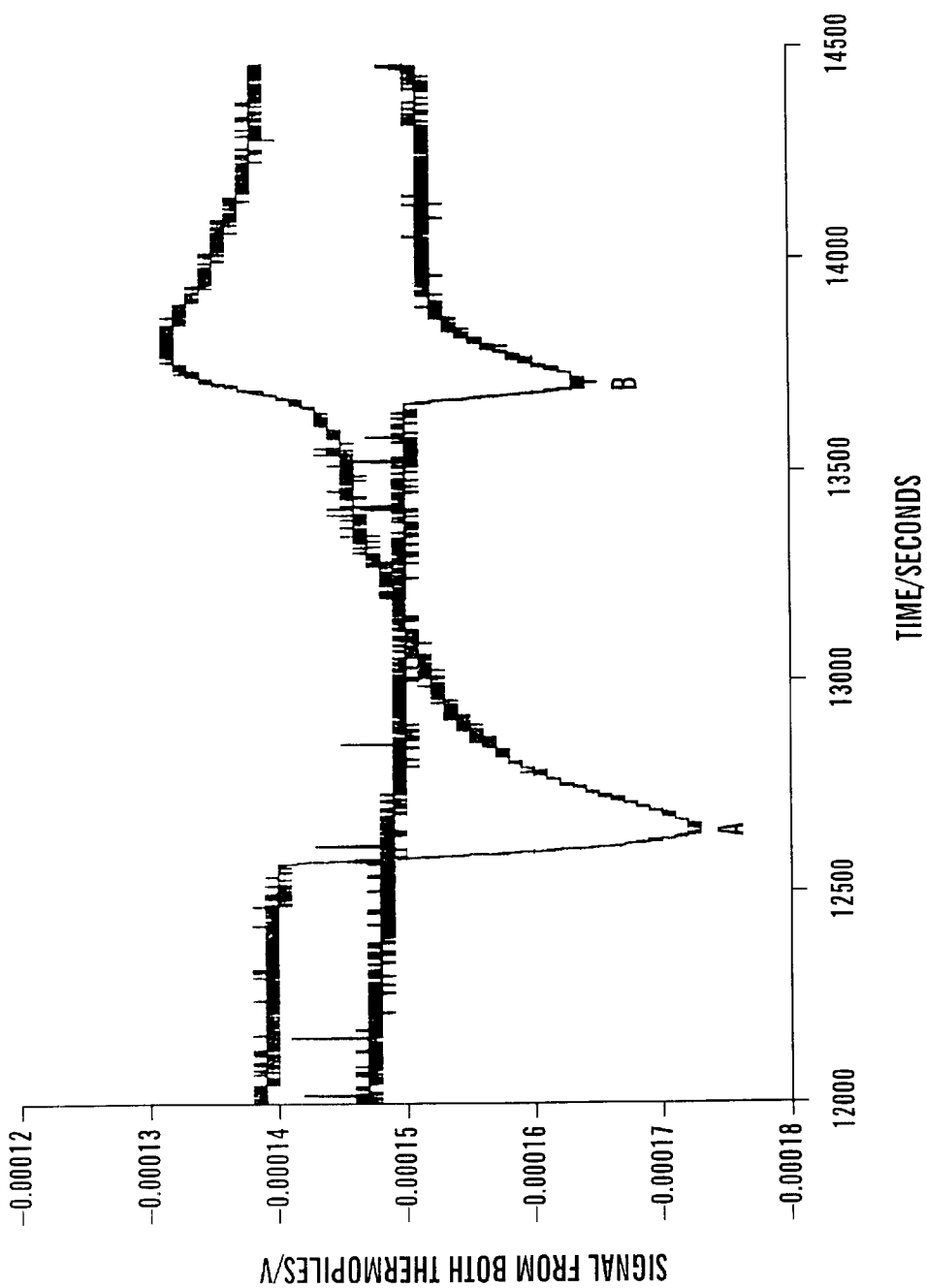
FIG. 20 shows diagrammatic representations for the heat flow sensors in the devices of FIG. 5 in response to the deposition of n-butanol vapor on the surface of one of the quartz crystal microbalances.

A further series of experiments showed definitively that the combined quartz crystal microbalance and heat flow sensor sample and reference devices respond in both channels to the adsorption and desorption of several organic vapors on the bare gold surface of each quartz crystal microbalance. The full time series from the quartz crystal microbalance and from each of the two heat flow sensors are shown in FIGS. 13 and 14, respectively. This set of experiments took about four hours to perform. A slight difference between event times in the quartz crystal microbalance trace and the heat flow sensor trace is due to a small difference in time scale calibrations for the two channels, which could be corrected by computer software, but was not corrected for these experiments. FIGS. 15 and 16 show the quartz crystal microbalance and heat flow sensor responses to 0.5 mL aliquots of toluene vapor injected in the gas flow to the left (signal A) and right (signal B) quartz crystal microbalance and heat flow sensor combination devices, respectively. FIGS. 17 and 18 show similar experiments with chloroform vapor. FIGS. 19 and 20 show the quartz crystal microbalance and heat flow sensor responses with n-butanol vapor.

Still another aspect of the present invention pertains to a mass and heat flow measurement apparatus comprising (i) a gas sample sensor comprising a first microresonator, a first heat flow sensor, and a heat sink coupled thermally to the first heat flow sensor, wherein the first heat flow sensor is thermally coupled to the first microresonator; and further wherein the first microresonator comprises a coated surface and is capable of measuring the changes in mass when a gas reacts with, is adsorbed, or is desorbed from the coated surface; and the first heat flow sensor is capable of measuring the flow of heat from the coated surface to the heat sink; (ii) a gas reference sensor comprising a second microresonator, a second heat flow sensor coupled thermally to the second microresonator, and a heat sink coupled thermally to the second microresonator; and, (iii) a chamber housing the gas sample and gas reference sensors, wherein the gas reference sensor is isolated from the gas in contact with the first microresonator; and further wherein the second microresonator is capable of measuring a reference signal relating to mass at a surface of the second microresonator, and the second heat flow sensor is capable of measuring a reference signal relating to the flow of heat from the surface of the second microresonator to the heat sink coupled thermally to the second heat flow sensor. In one embodiment, the chamber further comprises a gas input lead for introducing the gas into contact to the coated surface of the first microresonator and a gas output lead for removing the gas from contact to the coated surface of the first microresonator.

Yet another aspect of the present invention pertains to a mass and heat flow measurement system comprising (i) at least one mass and heat flow measurement gas sample sensor comprising a microresonator, a heat flow sensor coupled thermally to the microresonator, and a heat sink coupled thermally to the heat flow sensor, wherein the microresonator comprises a coated surface and generates data relating to the changes in mass on the coated surface of the microresonator arising from contacting the coated surface with a gas; and further wherein the heat flow sensor generates data relating to the changes in flow of heat from the coated surface to the heat sink from contacting the coated surface with the gas; (ii) at least one mass and heat flow measurement gas reference sensor comprising a reference microresonator, a reference heat flow sensor coupled thermally to the reference microresonator, and a heat sink coupled thermally to the reference heat flow sensor, wherein the microresonator of the gas reference sensor is not in contact with the gas in contact with the microresonator of the gas sample sensor; and further wherein the reference microresonator generates data relating to the changes in mass on a surface of the reference microresonator, and the reference heat flow sensor generates data relating to the changes in flow of heat from the surface of the reference microresonator to the heat sink coupled thermally to the reference heat flow sensor; and, (iii) a measurement instrument capable of correlating the data from the gas sample and gas reference sensors so as to provide measurement of the changes in mass on the coated surface of the microresonator of the gas sample sensor and the flow of heat from the coated surface to the heat sink coupled thermally to the heat flow sensor of the gas sample sensor. In one embodiment, the system further comprises a gas input lead for introducing the gas into contact to the coated surface of the microresonator of the gas sample sensor and a gas output lead for removing the gas from contact to the coated surface of the microresonator of the gas sample sensor.

Another aspect of the present invention pertains to a heat flow measurement apparatus comprising (i) a liquid sample sensor comprising a first microresonator, a first heat flow sensor, and a heat sink coupled thermally to the first heat flow sensor, wherein the first heat flow sensor is thermally coupled to the first microresonator; and further wherein the first microresonator is capable of measuring a signal relating to mass at a surface of the first microresonator, and the first heat flow sensor is capable of measuring the flow of heat from a liquid sample disposed on the first microresonator to the heat sink; (ii) a liquid reference sensor comprising a second microresonator, a second heat flow sensor coupled thermally to the second microresonator, and a heat sink coupled thermally to the second microresonator; and, (iii) a chamber housing the liquid sample and liquid reference sensors, wherein the liquid reference sensor is isolated from the liquid sample in contact with the first microresonator; and further wherein the second microresonator is capable of measuring a reference signal relating to mass at a surface of the second microresonator, and the second heat flow sensor is capable of measuring a reference signal relating to the flow of heat from the surface of the second microresonator to the heat sink coupled thermally to the second heat flow sensor. In one embodiment of the heat flow apparatus of this invention, the chamber further comprises a liquid input lead for introducing the liquid sample into contact to the first microresonator. In one embodiment, the first microresonator is capable of measuring the mass of the liquid sample in contact with the first microresonator.

Still another aspect of this invention pertains to a heat flow measurement system comprising (i) at least one heat flow measurement liquid sample sensor comprising a microresonator, a heat flow sensor coupled thermally to the microresonator, and a heat sink coupled thermally to the heat flow sensor, wherein the microresonator is capable of measuring a signal relating to mass at a surface of the microresonator; and further wherein the heat flow sensor generates data relating to the changes in the flow of heat from a liquid sample to the heat sink from contacting the microresonator with the liquid sample; (ii) at least one heat flow measurement liquid reference sensor comprising a reference microresonator, a reference heat flow sensor coupled thermally to the reference microresonator, and a heat sink coupled thermally to the reference heat flow sensor, wherein the microresonator of the reference sensor is not in contact with the liquid sample in contact with the microresonator of the liquid sample sensor; and further wherein the reference microresonator is capable of measuring a reference signal relating to mass at a surface of the reference microresonator, and the reference heat flow sensor generates data relating to the changes in flow of heat from the surface of the reference microresonator to the heat sink coupled thermally to the reference heat flow sensor; and, (iii) a measurement instrument capable of correlating the data from the liquid sample and liquid reference sensors so as to provide measurement of the flow of heat from the liquid sample to the heat sink coupled thermally to the heat flow sensor of the liquid sample sensor. In one embodiment of the heat flow measurement system of the present invention, the system further comprises a liquid input lead for introducing the liquid sample to the microresonator of the liquid sample sensor. In one embodiment, the microresonator of the liquid sample sensor generates data relating to the changes in mass on a surface of the microresonator of the liquid sample sensor, which data arises from contacting the microresonator of the liquid sample sensor with the liquid sample; wherein the reference microresonator generates data relating to the changes in mass on a surface of the reference microresonator; and further wherein the measurement instrument is capable of correlating the data from the liquid sample and liquid reference sensors so as to further provide measurement of the mass of the liquid sample. In one embodiment, the mass of the liquid sample is known.

Applications of the Mass and Heat Apparatus and System to Measure Enthalpies of Sublimation In his review of trends in isothermal microcalorimetry in *Chemical Society Reviews*, Volume 1997, pages 79–86 (1997), Wadso states:

"There is a strong need for enthalpy of sublimation data for substances with very low vapor pressures, for example in connection with investigations of biothermodynamic model systems. However, very little development work and few measurements have been reported during the last few decades in vaporization/sublimation calorimetry. More advanced microcalorimetric techniques are much needed in this field."

Isothermal heat conduction calorimetry has been used to measure $\Delta H_{sub}$ for compounds with vapor pressures as low as $10^{-6}$ torr, as, for example, described in *Chemical Scripta*, Vol. 1, pages 103–111 (1971) by Morawetz and in *Thermochimica Acta*, Vol. 115, pages 153–165 (1987) by Sabbah et al. Knudsen effusion methods, which use the Clausius-Clapeyron equation to derive $\Delta H_{sub}$ from the variation of vapor pressure with temperature, as, for example, described in *J. Chem. Thermo.*, Vol. 27, pages 1261–1266 (1995) by Torres et al, have been used on compounds with vapor pressures in the same range. Because many interesting organic and biological substances have room temperature vapors lower than these limits, their enthalpies of sublimation have not yet been measured. Yet for an accurate determination of the Gibbs free energy of formation, the heat of sublimation must be known. The energetics of formation of such substances in the gas phase is of great importance in determining the chemical reactivity of the substance, and in comparing with quantum chemical calculations of the same quantity.

The microresonator and heat flow sensor combination device can be used to measure sublimation enthalpies of quite non-volatile materials. The relationship between the sublimation rate of a solid, $\sigma$(moles m$^{-2}$ s$^{-1}$), and its vapor pressure was first presented by Langmuir in Physical Review, Vol. 2, 329 (1913), as follows:

$$\sigma = P_{eq}/\sqrt{2\pi MRT}$$

Here, $P_{eq}$ is the equilibrium vapor pressure of the solid, M is its molar mass, R is the gas constant, and T is the absolute temperature. For the hypothetical solid described above, with a sublimation enthalpy of 50 kJ/mol and a molar mass of 200 g/mole, a surface area of 1 cm$^2$ will lose mass at the rate of 1.0 ng/sec if the vapor pressure of the solid is $2.0 \times 10^{-8}$ torr.

From the design perspective, it is helpful to use as large a diameter, D, for the microresonator as possible, since this permits a larger sample area ($\pi d2/4$, FIG. 4) and thus a larger thermal signal. Of importance in evacuating the microresonator and heat flow sensor combination apparatus and system is the nature of the piezoelectric substrate-to-metal contact, such as quartz-to-metal contact, (for example, o-ring, direct contact without bonding, or a high-vacuum seal), since the underside of the quartz crystal must not be subject to adsorbing vapors from the sample.

Applications of the Mass and Heat Flow Apparatus and System to Energy-Sensitive Chemical Sensors There is a large and actively growing literature on specific and sensitive chemical sensors based on surface-coated microresonator, such as quartz crystal oscillator, technology. For example, *Sensors and Actuators* B, Vol. 18–19, pages 429–433 (1994) by Hartmann et al., describes use of a quartz crystal microbalance coated with polymers, with lipophilic compounds, with calix-n-arenes, with complex formers, and with a monomolecular layer to explore the sensitivity and selectivity of quartz crystal microbalance-based gas sensors. Also, for example, *Sensors and Actuators* B, Vol. 34, pages 356–360 (1996) by Zhou et al., describes coating both a quartz crystal microbalance and a separate calorimetric transducer with a cycloaliphatic poly(ether urethane) to detect organic solvent vapors. However, there has been no report of a combined microresonator and heat flow sensor combination used as a gas sensor. Since the combined microresonator and heat flow sensor combination apparatus and system give a real-time measurement of the molar heat of adsorption, it has a powerful additional measurement dimension which should provide further selectivity for gas sensors. There are also many fundamental problems of interest to study with the microresonator and heat flow sensor combination apparatus and system, such as, for example, the continuous variation in molar enthalpy with increasing surface coverage from adsorption of a monolayer to condensation of the bulk solid.

Applications of the Mass and Heat Flow Apparatus and System to Measuring the Binding Enthalpy of Water in Biological Materials If a protein in solution is coated on the microresonator, such as a quartz crystal microbalance, at high water vapor pressure or relative humidity, the decrease in mass and the heat required for evaporation of water may be studied by varying the partial pressure of water in the gas above the surface. At first, one should expect the thermal signal to be almost the same as the enthalpy of vaporization of water itself, but as more and more water is removed, the binding energy per water molecule should change to that more representative of protein molecule-water interaction energies. Such studies should help to elucidate the binding energetics of water in any biological material.

Other Applications of the Mass and Heat Flow Apparatus and System

The microresonator and heat flow sensor combination apparatus and system measure simultaneously and continuously, with high sensitivity (nanogram in mass, submicrowatt in heat flow), the change in mass and heat flow at a small gas-solid interface of, for example, about 1 $cm^2$, due to chemical processes such as evaporation or condensation, adsorption or desorption, or gas-surface reactions. Other potential applications of the microresonator and heat flow sensor combination apparatus and system include, but are not limited to, the study of:

(a) the hydration and dehydration of films of proteins and other biomolecules deposited on solid substrates. These films are used, for example, in biosensors, diagnostic immunoassays, the separation of proteins by chromatography, and as models for biological and biocompatible membranes and surfaces;

(b) the energetics of intermolecular interactions at the surface of polymer films and other organic surfaces important in adhesion, lubrication, wetting, and corrosion; and, (c) the energetics of the drying and curing of both water-based and organic solvent-based paints and finishes.

Methods for Measuring Mass and Heat Flow of Samples

Another aspect of the present invention pertains to a method for measuring the mass of a sample and the flow of heat from the sample to a heat sink, which method comprises the steps of: (i) contacting the sample with a mass and heat flow measurement system, as described herein; (ii) obtaining data from both the sample and reference sensors of the mass and heat flow measurement system of the present invention; and, (iii) determining the mass of the sample and the flow of heat from the sample to the heat sink coupled thermally to the heat flow sensor of the sample sensor. In one embodiment, the sample is a solid sample, and, preferably, the method of this invention measures the enthalpy of sublimation of the solid sample.

As described herein, in the apparatus, systems, and methods of the present invention, the change in mass of the sample is measured by a change in the frequency of the piezoelectric substrate of the microresonator, and the change in the flow of heat from the sample to the heat sink is typically measured by a change in the voltage output of the heat flow sensor. Suitable electrical circuitry and data collection and correlation equipment and methods for these measurements include, but are not limited to, those described for microresonators in the afore-mentioned references by Grate et al., Alder et al., McCallum, and Lu et al., and for heat flow sensors in the afore-mentioned review article by Wadso and references therein.

Another aspect of the present invention pertains to a method for measuring the change in mass and flow of heat from a coated surface to a heat sink when a gas reacts with, is adsorbed, or is desorbed from the coated surface, which method comprises the steps of: (i) contacting the gas with a mass and heat flow gas measurement system, as described herein; (ii) obtaining data from both the gas sample and gas reference sensors of the mass and heat flow gas measurement system of this invention; and, (iii) determining the changes in mass and the flow of heat from the coated surface of the microresonator of the gas sample sensor to the heat sink coupled thermally to the heat flow sensor of the gas sample sensor, which changes arise when the gas reacts with, is adsorbed, or is desorbed from the coated surface. In one embodiment of the method, the mass and heat flow gas measurement system further comprises a gas input lead for introducing the gas to the microresonator of the gas sample sensor and a gas output lead for removing the gas from contact to the microresonator of the gas sample sensor. In one embodiment, the method measures the molar heat of adsorption of the gas, and, preferably, the molar heat of adsorption is measured in real time. In one embodiment, the reference microresonator comprises a coated surface. In one embodiment, the coated surface of the reference microresonator comprises the same coating as the coated surface of the microresonator of the gas sample sensor. In one embodiment, the method measures the molar heat of reaction of the gas with the coated surface, and, preferably, the molar heat of reaction is measured in real time. In one embodiment, the method measures the molar heat of desorption of the gas, and, preferably, the molar heat of desorption is measured in real time. In one embodiment, the microresonator of the gas sample sensor and the reference microresonator are selected from the group of microresonators consisting of: bulk acoustic wave sensors, quartz crystal microbalances, surface acoustic wave sensors, flexural plate wave sensors, and acoustic plate mode sensors. In a preferred embodiment, the microresonator of the gas sample sensor and the reference microresonator are quartz crystal microbalances.

Another aspect of the present invention pertains to a method for measuring the change in the flow of heat from a liquid sample to a heat sink, which method comprises the steps of: (i) contacting the liquid sample with a heat flow measurement system, as described herein; (ii) obtaining data from both the liquid sample and liquid reference sensors of the heat flow measurement system of this invention; and, (iii) determining the flow of heat from the liquid sample to the heat sink coupled thermally to the heat flow sensor of the liquid sample sensor. In one embodiment, the heat flow measurement system further comprises a liquid input lead for introducing the liquid sample to the microresonator of the liquid sample sensor. In one embodiment, the microresonator of the liquid sample sensor generates data relating to the changes in mass on a surface of the microresonator of the liquid sample sensor, which data arises from contacting the microresonator of the liquid sample sensor with the liquid sample; wherein the reference microresonator generates data relating to the changes in mass on a surface of the reference microresonator; and further wherein the measurement instrument is capable of correlating the data from the liquid sample and liquid reference sensors so as to further provide measurement of the mass of the liquid sample. In one embodiment, the mass of the liquid sample is known. In one embodiment, the method measures the molar heat of evaporation of the liquid sample. In one embodiment, the microresonator of the liquid sample sensor comprises a coated surface, and, preferably, the reference microresonator also comprises a coated surface, and, most preferably, the coated surface of the reference microresonator comprises the same coating as the coated surface of the microresonator of the liquid sample sensor. In one embodiment, the microresonator of the liquid sample sensor and the reference microresonator are selected from the group of microresonators consisting of: bulk acoustic wave sensors, quartz crystal microbalances, surface acoustic wave sensors, flexural plate wave sensors, and acoustic plate mode sensors. In a preferred embodiment, the microresonator of the liquid sample sensor and the reference microresonator are quartz crystal microbalances.

While the invention has been described in detail and with reference to specific embodiments thereof, it will be apparent to one skilled in the art that various changes and modifications can be made without departing from the spirit and scope thereof.

What is claimed is:

1. A measurement apparatus comprising:
   (a) a liquid sample sensor comprising a first microresonator, a first heat flow sensor, and a heat sink coupled thermally to said first heat flow sensor, wherein said first heat flow sensor is thermally coupled to said first microresonator; and further wherein said first microresonator is capable of measuring a signal relating to one or more properties at a surface of said first microresonator, and said first heat flow sensor is capable of measuring the flow of heat from a liquid sample disposed on said surface of said first microresonator to the heat sink; and
   (b) a liquid reference sensor comprising a second microresonator, a second heat flow sensor coupled thermally to said second microresonator, and a heat flow sink coupled thermally to said second heat flow sensor;
   wherein said liquid reference sensor is isolated from the liquid sample in contact with said first microresonator; and further wherein said second microresonator is capable of measuring a reference signal relating to said one or more properties at a surface of said second microresonator and said second heat flow sensor is capable of measuring a reference signal relating to the flow of heat from said surface of said second microresonator to the heat sink coupled thermally to said second heat flow sensor.

2. The apparatus of claim 1, wherein said apparatus further comprises a liquid input lead for introducing said liquid sample into contact to said first microresonator.

3. The apparatus of claim 1, wherein said first microresonator is capable of measuring the mass of the liquid sample in contact with said first microresonator.

4. The apparatus of claim 1, wherein said first heat flow sensor is capable of simultaneously measuring the flow of heat from the liquid sample to said heat sink coupled thermally to said first heat flow sensor, in real time with the measurement of said one or more properties of the liquid sample by said first microresonator; and said reference sensor is capable of simultaneously measuring the reference signal relating to said one or more properties at said surface of said second microresonator and the reference signal relating to the flow of heat from said surface of said second microresonator, in real time with said measurement by said first microresonator and in real time with the measurement of the flow of heat by said first heat flow sensor.

5. The apparatus of claim 1, wherein one of said one or more properties of the liquid sample measured by said first microresonator is selected from the group of properties consisting of mass, liquid density, and liquid viscosity.

6. The apparatus of claim 1, wherein said first and second microresonators are selected from the group of microresonators consisting of bulk acoustic wave sensors, quartz crystal microbalances, surface acoustic wave sensors, flexural plate wave sensors, and acoustic plate mode sensors.

7. A measurement system comprising:
   (a) one or more liquid sample sensors comprising a microresonator, a heat flow sensor coupled thermally to said microresonator, and a heat sink coupled thermally to said heat flow sensor, wherein said microresonator is capable of measuring a signal relating to one or more properties at a surface of said microresonator; and further wherein said heat flow sensor generates data relating to the changes in flow of heat from a liquid sample to the heat sink from contacting a surface of said microresonator with the liquid sample;
   (b) one or more liquid reference sensors comprising a reference microresonator, a reference heat flow sensor coupled thermally to said reference microresonator, and a heat sink coupled thermally to said reference heat flow sensor, wherein the reference microresonator of said one or more liquid reference sensors is not in contact with the liquid sample in contact with the microresonator of said one or more liquid sample sensors; and further wherein said reference microresonator is capable of measuring a reference signal relating to said one or more properties at a surface of said reference microresonator, and said reference heat flow sensor generates data relating to the changes in flow of heat from the surface of said reference microresonator to the heat sink coupled thermally to said reference heat flow sensor; and
   (c) a measurement instrument capable of correlating the data from said one or more liquid sample sensors and from said one or more liquid reference sensors so as to provide measurement of said one or more properties at the surface of said microresonator and of the flow of heat from the liquid sample to the heat sink coupled thermally to said heat flow sensor of said one or more liquid sample sensors.

8. The system of claim 7, wherein said system further comprises a liquid input lead for introducing the liquid sample to the microresonator of said one or more liquid sample sensors.

9. The system of claim 7, wherein the microresonator of said one or more liquid sample sensors generates data relating to the changes in mass on a surface of the microresonator of said one or more liquid sample sensors, which data arises from contacting the surface of the microresonator of said one or more liquid sample sensors with the liquid sample; wherein said one or more liquid reference sensors generate data relating to the changes in mass on a surface of said reference microresonator; and further wherein said measurement instrument is capable of correlating the data from said one or more liquid sample sensors and from said one or more liquid reference sensors so as to provide measurement of the mass of the liquid sample.

10. The system of claim 7, wherein the mass of said liquid sample at the time of contacting the microresonator of said one or more liquid sample sensors with the liquid sample is known.

11. The system of claim 7, wherein one of said one or more properties of the liquid sample measured by the microresonator of said one or more liquid sample sensors is selected from the group of properties consisting of mass, liquid density, and liquid viscosity.

12. A method for measuring a liquid sample, which method comprises the steps of:
   (a) contacting a liquid sample with a measurement system which comprises:
      (i) one or more liquid sample sensors comprising a microresonator, a heat flow sensor coupled thermally to said microresonator, and a heat sink coupled thermally to said heat flow sensor, wherein said microresonator is capable of measuring a signal relating to one or more properties at a surface of said microresonator; and further wherein said heat flow sensor generates data relating to the changes in flow of heat from the liquid sample to the heat sink from contacting a surface of said microresonator with the liquid sample;

(ii) one or more liquid reference sensors comprising a reference microresonator, a reference heat flow sensor coupled thermally to said reference microresonator, and a heat sink coupled thermally to said reference heat flow sensor, wherein the reference microresonator of said one or more reference sensors is not in contact with the liquid sample in contact with the microresonator of said one or more liquid sample sensors; and further wherein said reference microresonator is capable of measuring a reference signal relating to said one or more properties at a surface of said reference microresonator, and said reference heat flow sensor generates data relating to the changes in the flow of heat from the surface of said reference microresonator to the heat sink coupled thermally to said reference heat flow sensor; and (iii) a measurement instrument capable of correlating the data from said one or more liquid sample sensors and from said one or more liquid reference sensors so as to provide measurement of said one or more properties at the surface of said microresonator and of the flow of heat from the liquid sample to the heat sink coupled thermally to said heat flow sensor of said one or more liquid sample sensors;

(b) obtaining said data from said one or more liquid sample sensors and from said one or more liquid reference sensors; and (c) determining said one or more properties of the liquid sample on the surface of said microresonator and the flow of heat from the liquid sample to the heat sink coupled thermally to the heat flow sensor of said one or more liquid sample sensors.

13. The method of claim 12, wherein said measurement system of step (a) further comprises a liquid input lead for introducing the liquid sample to the microresonator of said one or more liquid sample sensors.

14. The method of claim 12, wherein the microresonator of said one or more liquid sample sensors generates data relating to the changes in mass on a surface of the microresonator of said one or more liquid sample sensors, which data arises from contacting the surface of the microresonator of said one or more liquid sample sensors with the liquid sample; wherein said one or more liquid reference sensors generates data relating to the changes in mass on a surface of said reference microresonator; and further wherein said measurement instrument is capable of correlating the data from said one or more liquid sample sensors and from said one or more liquid reference sensors so as to provide measurement of the mass of the liquid sample.

15. The method of claim 12, wherein the mass of the liquid sample at the time of contacting the microresonator of said one or more liquid sample sensors with the liquid sample in step (a) is known.

16. The method of claim 12, wherein one of said one or more properties of the liquid sample measured by the microresonator of said one or more liquid sample sensors is selected from the group of properties consisting of mass, liquid density, and liquid viscosity.

17. The method of claim 14, wherein said method measures a molar heat of evaporation of the liquid sample.

18. The method of claim 12, wherein the microresonator of at least one of said one or more liquid sample sensors comprises a coated surface.

19. The method of claim 18, wherein the reference microresonator of at least one of said one or more liquid reference sensors comprises a coated surface.

20. The method of claim 19, wherein the coated surface of the reference microresonator comprises the same coating as the coated surface of the microresonator of said at least one of said one or more liquid sample sensors.

21. The method of claim 12, wherein the microresonator of said one or more liquid sample sensors and the reference microresonator of said one or more liquid reference sensors are selected from the group of microresonators consisting of bulk acoustic wave sensors, quartz crystal microbalances, surface acoustic wave sensors, flexural plate wave sensors, and acoustic plate mode sensors.

22. The method of claim 12, wherein the microresonator of said one or more liquid sample sensors and the reference microresonator of said one or more liquid reference sensors are quartz crystal microbalances.

* * * * *